(12) United States Patent
Arnal et al.

(10) Patent No.: US 7,905,825 B2
(45) Date of Patent: Mar. 15, 2011

(54) PELVIC IMPLANTS AND RELATED METHODS

(75) Inventors: Kevin R. Arnal, Excelsior, MN (US); Sidney F. Hauschild, St. Paul, MN (US); Peter A. Jacobs, Minneapolis, MN (US); Suranjan Roychowdhury, Plymouth, MN (US)

(73) Assignee: AMS Research Foundation, Minnetonka, MN (US)

( * ) Notice: Subject to any disclaimer, the term of this patent is extended or adjusted under 35 U.S.C. 154(b) by 0 days.

(21) Appl. No.: 11/347,063

(22) Filed: Feb. 3, 2006

(65) Prior Publication Data

US 2006/0195011 A1    Aug. 31, 2006

Related U.S. Application Data

(60) Provisional application No. 60/650,208, filed on Feb. 4, 2005, provisional application No. 60/650,209, filed on Feb. 4, 2005, provisional application No. 60/659,714, filed on Mar. 8, 2005, provisional application No. 60/659,504, filed on Mar. 8, 2005, provisional application No. 60/677,457, filed on May 4, 2005, provisional application No. 60/683,185, filed on May 20, 2005, provisional application No. 60/650,207, filed on Feb. 4, 2005.

(51) Int. Cl.
*A61F 2/02* (2006.01)
(52) U.S. Cl. ....................................... 600/30
(58) Field of Classification Search ............. 600/29–30, 600/37; 604/246; 128/885, 889
See application file for complete search history.

(56) References Cited

U.S. PATENT DOCUMENTS

| | | | |
|---|---|---|---|
| 4,827,940 | A | 5/1989 | Mayer et al. |
| 5,112,344 | A | 5/1992 | Petros |
| 5,383,904 | A | 1/1995 | Totakura et al. |
| 5,531,783 | A | 7/1996 | Giele et al. |
| 5,611,515 | A | 3/1997 | Benderev et al. |
| 5,716,391 | A | 2/1998 | Grandjean |
| 5,842,478 | A | 12/1998 | Benderev et al. |
| 5,860,425 | A | 1/1999 | Benderev et al. |
| 5,899,909 | A | 5/1999 | Claren et al. |
| 6,039,686 | A | 3/2000 | Kovac |
| 6,042,534 | A | 3/2000 | Gellman et al. |
| 6,042,536 | A | 3/2000 | Tihon et al. |
| 6,110,101 | A | 8/2000 | Tihon et al. |
| 6,273,852 | B1 | 8/2001 | Lehe et al. |

(Continued)

FOREIGN PATENT DOCUMENTS

DE          20204669          9/2003

(Continued)

OTHER PUBLICATIONS

Rios, Luis, A.S., Male Perineal Sling with Autologous Aponeurosis and Bone Fixation—Description of a Technical Modification, Int'l Braz. J. Urol. vol. 29 (6), 524-527 (Nov.-Dec. 2003).

(Continued)

*Primary Examiner* — Charles A Marmor, II
*Assistant Examiner* — Christine D Hopkins
(74) *Attorney, Agent, or Firm* — Kimberly K. Baxter; Gregory L. Koeller

(57) ABSTRACT

Described are surgical implants that include a central support portion adapted to be positioned to support pelvic tissue, between mesh end portions adapted to be passed through body tissue, wherein edges of the end portions exhibit extensions that are resistant to deformation.

13 Claims, 19 Drawing Sheets

U.S. PATENT DOCUMENTS

| | | | |
|---|---|---|---|
| 6,382,214 B1 | 5/2002 | Raz et al. | |
| 6,406,423 B1 | 6/2002 | Scetbon | |
| 6,475,139 B1 | 11/2002 | Miller | |
| 6,478,727 B2 | 11/2002 | Scetbon | |
| 6,575,897 B1 | 6/2003 | Ory et al. | |
| 6,582,443 B2 | 6/2003 | Cabak et al. | |
| 6,612,977 B2 | 9/2003 | Staskin et al. | |
| 6,638,210 B2 | 10/2003 | Berger | |
| 6,638,211 B2 | 10/2003 | Suslian et al. | |
| 6,641,524 B2 | 11/2003 | Kovac | |
| 6,641,525 B2 | 11/2003 | Rocheleau et al. | |
| 6,652,450 B2 | 11/2003 | Neisz et al. | |
| 6,689,047 B2 | 2/2004 | Gellman | |
| 6,691,711 B2 | 2/2004 | Raz et al. | |
| 6,702,827 B1 | 3/2004 | Lund et al. | |
| 6,716,158 B2 * | 4/2004 | Raman et al. | 600/37 |
| 6,755,781 B2 | 6/2004 | Gellman | |
| 6,802,807 B2 | 10/2004 | Anderson et al. | |
| 6,808,486 B1 | 10/2004 | O'Donnell | |
| 6,884,212 B2 | 4/2005 | Theirfelder et al. | |
| 6,908,425 B2 | 6/2005 | Luscombe | |
| 6,911,002 B2 | 6/2005 | Fierro | |
| 6,911,003 B2 | 6/2005 | Anderson et al. | |
| 6,953,428 B2 * | 10/2005 | Gellman et al. | 600/29 |
| 6,981,944 B2 | 1/2006 | Jamiolkowski et al. | |
| 6,991,597 B2 | 1/2006 | Gellman et al. | |
| 7,025,063 B2 | 4/2006 | Snitkin et al. | |
| 7,037,255 B2 | 5/2006 | Inman et al. | |
| 7,070,556 B2 | 7/2006 | Anderson et al. | |
| 7,070,558 B2 | 7/2006 | Gellman et al. | |
| 7,083,568 B2 | 8/2006 | Neisz et al. | |
| 2002/0099258 A1 * | 7/2002 | Staskin et al. | 600/29 |
| 2002/0138025 A1 | 9/2002 | Gellman et al. | |
| 2002/0147382 A1 | 10/2002 | Neisz et al. | |
| 2002/0151909 A1 | 10/2002 | Gellman et al. | |
| 2002/0156489 A1 | 10/2002 | Gellman et al. | |
| 2003/0009181 A1 | 1/2003 | Gellman et al. | |
| 2003/0130670 A1 | 7/2003 | Anderson et al. | |
| 2003/0149333 A1 | 8/2003 | Alferness | |
| 2003/0199732 A1 | 10/2003 | Suslian et al. | |
| 2003/0220538 A1 | 11/2003 | Jacquetin | |
| 2004/0006353 A1 | 1/2004 | Bosley, Jr. et al. | |
| 2004/0087970 A1 | 5/2004 | Chu et al. | |
| 2004/0193215 A1 | 9/2004 | Harari et al. | |
| 2004/0230092 A1 | 11/2004 | Thierfelder et al. | |
| 2004/0231678 A1 | 11/2004 | Fierro | |
| 2004/0249240 A1 | 12/2004 | Goldmann et al. | |
| 2005/0004424 A1 | 1/2005 | Raz et al. | |
| 2005/0021086 A1 | 1/2005 | De Leval | |
| 2005/0027220 A1 | 2/2005 | Wagner et al. | |
| 2005/0038451 A1 | 2/2005 | Rao et al. | |
| 2005/0038452 A1 * | 2/2005 | Chu | 606/151 |
| 2005/0043580 A1 | 2/2005 | Watschke et al. | |
| 2005/0065395 A1 | 3/2005 | Mellier | |
| 2005/0075660 A1 | 4/2005 | Chu et al. | |
| 2005/0080317 A1 | 4/2005 | Merade | |
| 2005/0129733 A1 * | 6/2005 | Milbocker et al. | 424/423 |
| 2005/0131274 A1 | 6/2005 | Suslian et al. | |
| 2005/0143618 A1 | 6/2005 | Anderson et al. | |
| 2005/0245787 A1 | 11/2005 | Cox et al. | |
| 2005/0261545 A1 | 11/2005 | Gellman et al. | |
| 2005/0267325 A1 | 12/2005 | Bouchier et al. | |
| 2006/0009673 A1 * | 1/2006 | Chan | 600/29 |
| 2006/0195007 A1 | 8/2006 | Anderson et al. | |
| 2006/0195010 A1 | 8/2006 | Arnal et al. | |
| 2006/0235262 A1 | 10/2006 | Arnal | |
| 2006/0247490 A1 | 11/2006 | Merade et al. | |
| 2006/0287571 A1 | 12/2006 | Gozzi et al. | |

FOREIGN PATENT DOCUMENTS

| | | |
|---|---|---|
| EP | 0797962 | 10/1997 |
| EP | 1342450 | 9/2003 |
| EP | 1248567 | 3/2004 |
| EP | 1151722 | 8/2004 |
| WO | WO 98/35632 | 8/1998 |
| WO | WO 01/35863 | 5/2001 |
| WO | WO 01/93656 | 12/2001 |
| WO | WO 02/39890 | 5/2002 |
| WO | WO 02/069781 | 9/2002 |
| WO | WO 2004/012579 | 2/2004 |
| WO | WO 2004/096088 | 11/2004 |
| WO | WO 2005/018494 | 3/2005 |

OTHER PUBLICATIONS

Palma, "Readjustable Transobturator Sling, A Novel Sling Procedure for Male Urinary Incontinence," Urologia Internationalis, 73:354-356, Dec. 2004.

Bauer et al., The self-anchoring transobturator male sling to treat stress urinary incontinence in men: a new sling, a surgical approach and anatomical findings in a cadaveric study, BJU Int. vol. 95(9), pp. 1364-1366, 2005.

Pereya, "A Simplified Surgical Procedure for the Correction of Stress Incontinence in Women," West J. Surg., Obstetrics & Gynecology, pp. 223-226, Jul.-Aug. 1959.

Compression of the bulbar urethra by transobturator suburethral tape, Progres en Urologie, (abstract), 14(4) pp. 507-511, Sep. 2004.

D. Dargent et al., Pose d'un ruban sous uretral oblique par voie obturatrice dans le traitement de l'incontinence urinaire feminine, Gynecol. Obstet. Fertil., 30: 576-582 (2002).

Moir J., et al., "The Gauze-Hammock Operation," The Journal of Obstetrics and Gynaecology of the British Commonwealth, vol. 75, No. 1, pp. 1-9, Jan. 1968.

Dietz et al., "Mechanical Properties of Urogynecologic Implant Materials," 14, 239-243 (2003).

Iglesia et al., "The Use of Mesh in Gynecologic Surgery," 8:105-115 (1997).

* cited by examiner

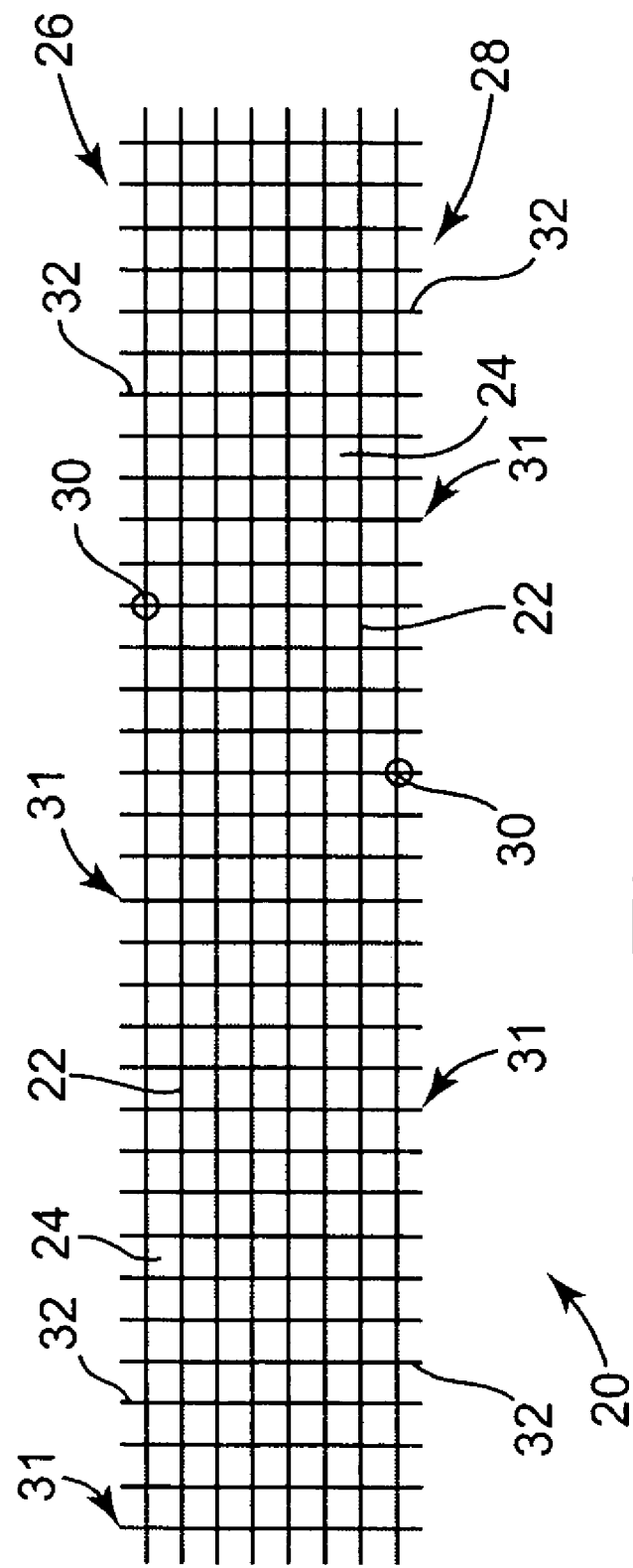

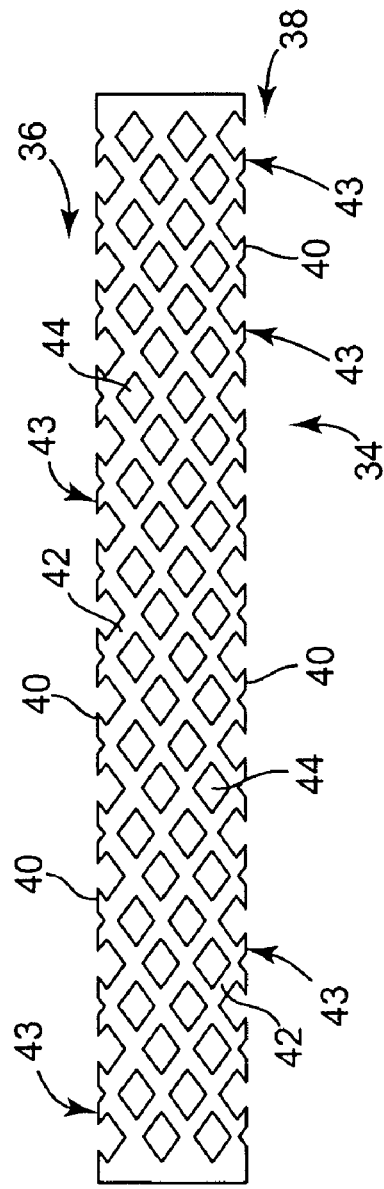
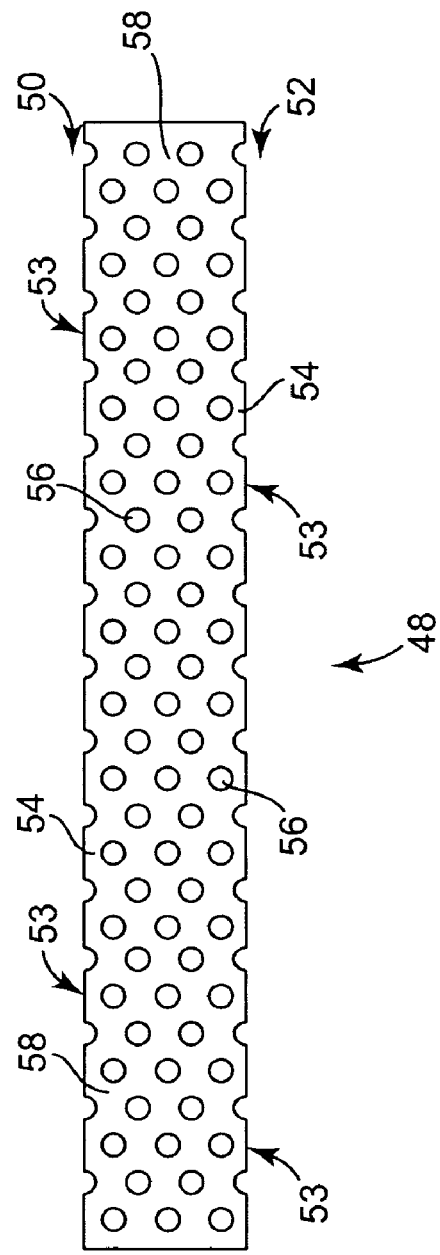
Fig. 3
Fig. 4

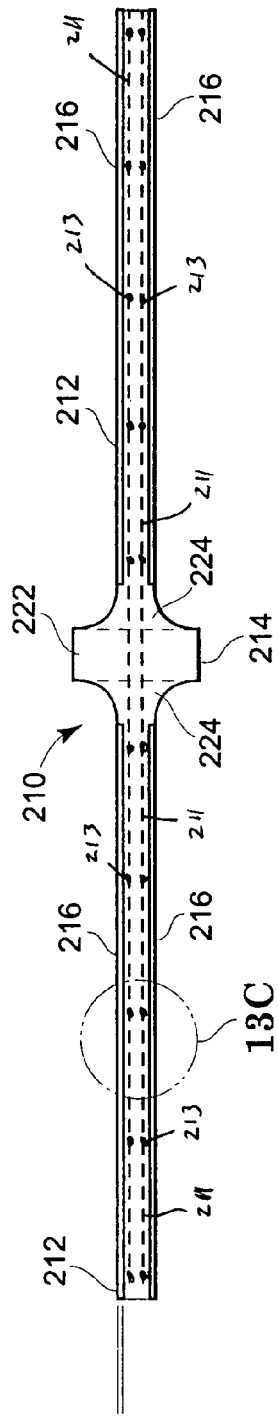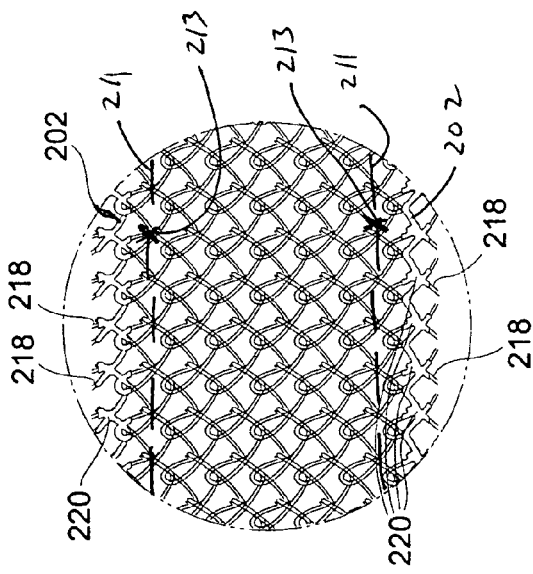
Fig. 13B
Fig. 13C

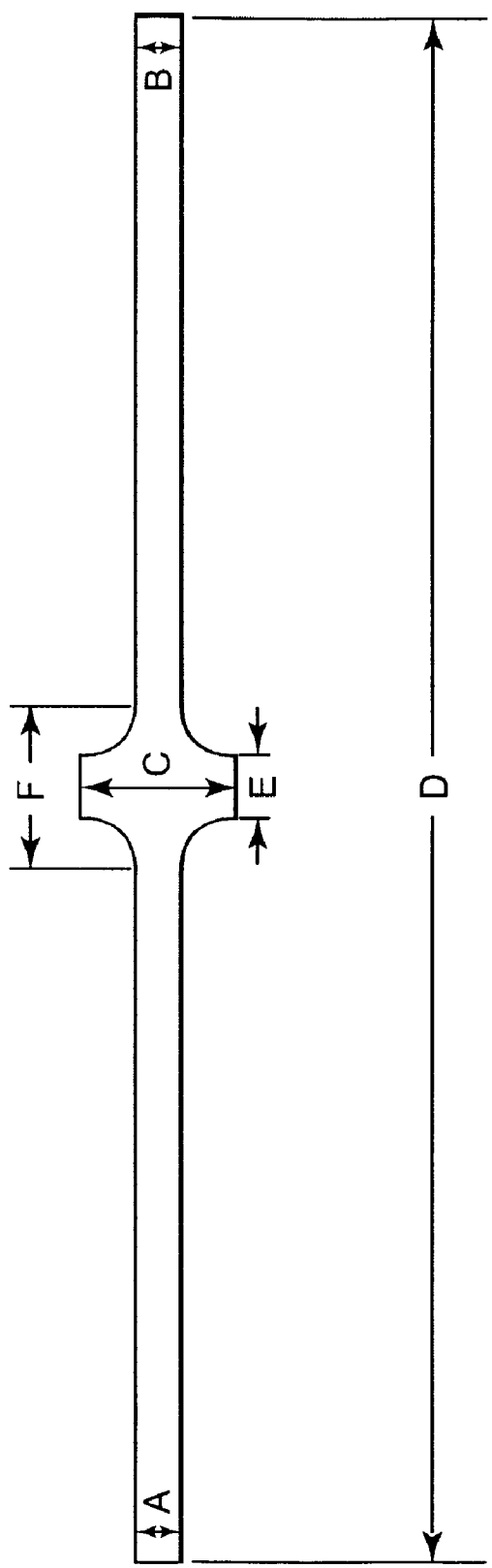

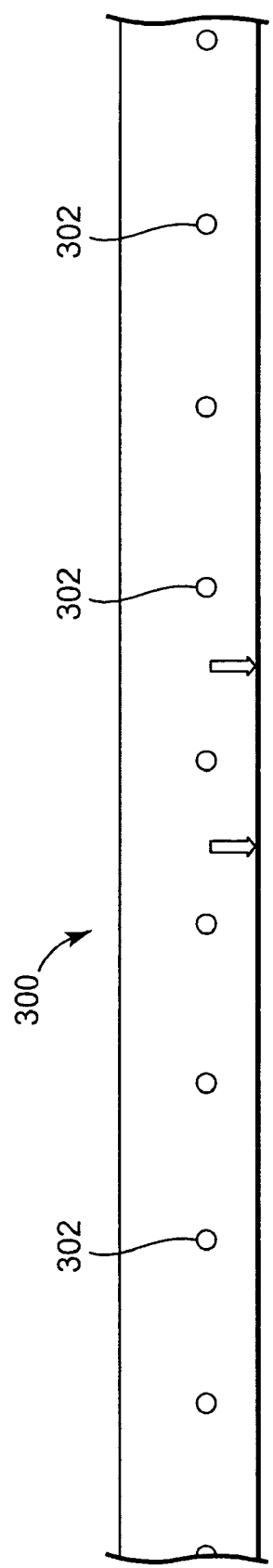

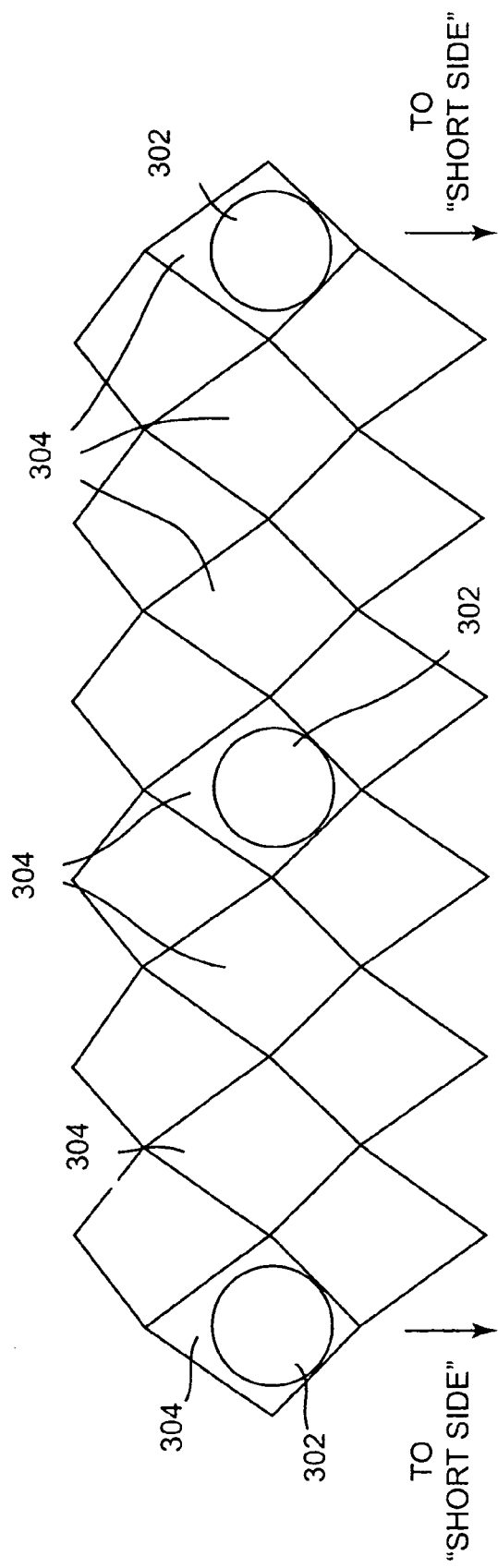

PELVIC IMPLANTS AND RELATED METHODS

PRIORITY CLAIM

The present non-provisional patent Application claims benefit under 35 USC §119(e) of United States Provisional Patent Applications having U.S. Ser. No. 60/650,208, filed on Feb. 4, 2005, by Arnal et al., and titled TRANSOBTURATOR SLING FOR MEN; U.S. Ser. No. 60/650,209, filed on Feb. 4, 2005, by Arnal et al., titled TRANSOBTURATOR SLING FOR MEN; U.S. Ser. No. 60/659,714, filed on Mar. 8, 2005, by Arnal et al., titled NEEDLE DESIGN FOR MALE TRANSOBTURATOR SLING; U.S. Ser. No. 60/659,504, filed on Mar. 8, 2005, by Arnal, titled NEEDLE DESIGN IMPROVEMENTS FOR MALE TRANSOBTURATOR SLING; U.S. Ser. No. 60/677,457, filed on May 4, 2005, by Hauschild et al., titled URETHRAL SLING OF KNITTED MESH WITH EDGE TREATMENT; U.S. Ser. No. 60/683,185, by Arnal, filed May 20, 2005, titled TRANSOBTURATOR SURGICAL SLING DELIVERY SYSTEM AND METHOD, and U.S. Ser. No. 60/650,207, filed on Feb. 4, 2005, by Rehder et al, titled TRANSOBTURATOR SLING FOR MEN, wherein the entirety of said provisional patent applications are incorporated herein by reference.

FIELD OF THE INVENTION

The invention relates to implantable articles designed to be implanted to support pelvic tissue such as the urethra or bladder, to treat incontinence or other pelvic conditions. Exemplary implants include a central support portion adapted to be positioned to support a pelvic tissue such as the urethra or bladder neck, with end portions or "extension portions" connected to and extending from the central support portion. The end portions are elongate and are designed to be passed through body tissue and to support the central support portion.

BACKGROUND

Incontinence is a condition characterized by involuntary loss of urine, beyond the individual's control, that results from the loss or diminution of the ability to maintain the urethral sphincter closed as the bladder fills with urine. Male or female stress urinary incontinence (SUI) occurs when the patient is physically or emotionally stressed. One cause for this condition is damage to the urethral sphincter or loss of support of the urethral sphincter, such as can occur in males after prostatectomy or following radiation treatment, or that can occur due to pelvic accidents and aging-related deterioration of muscle and connective tissue supporting the urethra. Other causes of male incontinence include bladder instability, detrusor external sphincter dyssynergia (DESD), rescection of the prostate, over-flowing incontinence, and fistulas.

The female's natural support system for the urethra is a hammock-like supportive layer composed of endopelvic fascia, the anterior vaginal wall, and the arcus tendineus (a distal attachment to the pubic bone). Weakening and elongation of the pubourethral ligaments and the arcus tendineus fascia pelvis, weakening of the endopelvic fascia and pubourethral prolapse of the anterior vaginal wall, and their complex interaction with intraabdominal forces, are all suspected to play a role in the loss of pelvic support for the urethra and subsequent hypermobility to an unnaturally low non-anatomic position, leading to urinary incontinence.

In general, continence is considered to be a function of urethral support and coaptation. For coaptation to successfully provide continence, the urethra must be supported and stabilized in its normal anatomic position. A number of surgical procedures and implantable medical devices have been developed over the years to provide urethral support and restore coaptation.

Females can also exhibit cystocele, a condition due to laxity of the pelvic floor wherein the bladder extrudes out and downwards causing SUI. The severity of this bladder collapse is rated between Grades one through four. In Grade four cystocele, the bladder extrudes out of the vaginal opening. The treatment of choice for this condition includes the reduction or closing of the pelvic floor opening from which the bladder descends using sutures. Further surgical procedures and implantable medical devices have been developed to correct cystocele by supporting the bladder.

Currently, incontinence treatments of choice involve implantation of a Kaufman Prosthesis, an artificial sphincter (such as the AMS-800 Urinary Control System available from American Medical Systems, Inc.), or a urethral sling procedure in which a urethral sling is inserted beneath the urethra and advanced in the retropubic space, and perforating the abdominal fascia. Peripheral portions of the elongated urethral sling are affixed to bone or body tissue, and a central support portion of the elongated urethral sling extends under the urethra or bladder neck to provide a platform that compresses the urethral sphincter, limits urethral distention, and pelvic drop, and thereby improves coaptation.

Male and female urethral sling procedures are disclosed in commonly assigned U.S. Pat. Nos. 6,382,214 and 6,652,450, for example, and further female urethral sling procedures are described in commonly assigned U.S. Pat. No. 6,641,524, for example, and publications and patents cited therein. Implantation of certain urethral slings involves the use of delivery systems configured for and techniques that involve transvaginal, transobturator, supra-pubic and pre-pubic exposures or pathways.

In further surgical approaches disclosed, for example, in commonly assigned U.S. Patent Application Publication Nos. 2005/0043580 and 2005/0065395 (the entireties of each of these being incorporated herein by reference), elongated self-fixating urethral slings are implanted for treating female prolapse by use of a pair of sling implantation instruments or tools. The sling implantation tools comprise a handle with an elongated needle portion terminating in a needle distal end adapted to be coupled to free ends of the urethral sling and have mirror image right and left handed needle shapes. The sling implantation tools disclosed in the above-referenced 2005/0043580 publication have a curvature in a single plane and correspond generally to the BioArc™ SP and SPARC™ single use sling implantation tools sold by American Medical Systems, Inc., in a kit with an elongated urethral sling. The sling implantation tools disclosed in the above-referenced 2005/0065395 publication have a curvature in 3-dimensional space and correspond generally to the BioArc™ TO and MONARC™ single use sling implantation tools sold by American Medical Systems, Inc., in a kit with an elongated urethral sling.

In an exemplary sling implantation tool for females, the needle portion has a proximal straight portion extending from the handle and a distal shaped portion terminating in a needle distal end. The needle portion is sized and shaped so that the distal end may initially be moved through an abdominal incision adjacent to the obturator foramen and advanced along the posterior surface of one of the right and left posterior ischiopubic pubic ramus of the pelvic girdle spaced from the bladder. The advancement is continued toward the obturator membrane of the obturator foramen, through the obturator membrane toward the region of the patient's ischial spine, and then toward a vaginal incision in the region of the vaginal apex. The surgeon uses a learned wrist motion of the hand grasping the handle, and pressure feedback felt through the handle, to guide advancement. Also, the surgeon may palpate the vaginal wall with the fingers of the free hand to locate the needle tip and guide the tip toward and through the vaginal incision to expose the needle tip. The procedure is repeated using the other of the right and left hand sling implantation tools to advance the needle tip through a second skin incision and the other of the respective right and left obturator membranes to expose both needle tips through a vaginal incisions. In this way, right and left subcutaneous transobturator pathways are formed between the abdominal skin and vaginal incisions and extending through the right and left obturator foramen and connective tissue attached to the right and left posterior ischiopubic pubic ramus of the pelvic girdle. This procedure is preformed without visualization of the needle tip, and care must be taken to avoid deviating posteriorly and penetrating the bladder and to otherwise avoid damaging any of the obturator nerves, the superficial epigastric vessel, the inferior epigastric vessel, the external iliac artery and the internal iliac artery.

Right and left end portions of the elongated urethral sling are then drawn through the respective right and left tissue pathways as further described in the above-referenced 2005/0043580 and 2005/0065395 publications. Generally speaking, the free ends of the elongated urethral sling are each coupled to the needle distal ends, and end portions of the urethral sling are drawn through the pathways to draw a central support portion against the urethra to provide support. The free ends of the elongated urethral slings can include dilating connectors for connecting with the needle distal ends so that the pathways are dilated as the connectors are drawn through. The dilating connectors are drawn out through the abdominal skin incisions (lateral incisions) and are severed from the urethral sling. During the passage, a detachable protective sheath encases the right and left end portions, and the protective sheath is detached and withdrawn over the end portions exposing the urethral sling mesh to body tissue. The ends of the urethral sling may be optionally sutured to subcutaneous tissue layers. Tissue ingrowth into the mesh pores stabilizes the urethral sling chronically. Similar procedures for installing an elongated urethral sling to support the male urethra to alleviate incontinence are described in U.S. Pat. No. 6,652,450.

At least the proximal portions of the urethral sling are typically formed of an open pore mesh that is woven or knitted from mesh strands of a variety of biocompatible materials. The central support portion can also be formed of the same open pore mesh, and the central and end portions can be formed of a single elongated open pore mesh. Alternately, the central support portion may be formed of another material that is sewn to or otherwise attached to ends of the end portions. The portions of the urethral sling formed of open pore mesh can be fabricated by weaving or braiding or knitting a bolt of open pore mesh and then cutting strips of the appropriate length and width from the bolt. Cutting is carefully controlled to extend through the centers of mesh pores so that the edges of the end portions and the central support portion, if formed integrally with the end portions, constitute severed strands that would otherwise bound mesh pores.

A great deal of strain is placed on the end portions of the elongated urethral slings, causing them to stretch longitudinally as they are drawn through the pathways formed by the instruments. The open pores of the mesh of the proximal portions can become distorted in the process, such that pores may be narrowed or closed, inhibiting effective tissue ingrowth. Consequently, it has been found desirable to stabilize or tension the proximal portions to prevent undue stretching and elongation by adding at least one inextensible thread or tensioning suture extending from the central support portion to the free ends of the right and left proximal ("end") portions. U.S. Pat. No. 6,652,450 describes a wide variety of resorbable or permanent tensioning sutures and techniques of fixing the tensioning suture to the open pore mesh of the right and left proximal portions.

The interaction of tissue with the severed strands along the sides of the end portions is also important in effecting fixation with tissue to maintain the appropriate tension of the central support portion against the urethra or bladder neck. It would be desirable for severed strands along edges of an implant to not become pressed out of the way, but remain extending outward and away from the intact pores of the open pore mesh. Consequently, it would be desirable to construct a urethral sling to advantageously maintain the shape of the urethral sling drawn through a tissue pathway and promote mechanical engagement with body tissue to aid in obtaining and maintaining tension.

SUMMARY

Described herein are surgical implants that have structure or functional features that improve performance of an installed implant, either during or after implantation. For example, described are implants that exhibit increased resistance to movement through tissue. These implants can include reinforced edge extensions. The implants include "end" or "extension" portions that extend from a central support portion. The end portions can be of an open pore material prepared from a film, mesh, or other suitable material. Edge extensions can be reinforced by various different structures of a film or mesh or by treatment of a film or mesh, such as by heat treatment of an end portion, or by addition of a reinforcing material such as a reinforcing strand adjacent to edge extensions or a reinforcing coating that contacts edge extensions. The reinforcement can be located on the edge extensions; adjacent to the edge extensions but not on the edge extensions; or, in combination, on the edge extensions and adjacent to the edge extensions.

A reinforcement may be formed in a porous material at any useful time before, during, or after formation of the porous material into a desired size and shape of an extension portion. For instance, a reinforcing strand, reinforcing weave or knot pattern, reinforcing coating, or reinforcing heat treatment, may be incorporated into a porous material prior to cutting or forming the porous material to a size and shape of an end portion or surgical implant, or after cutting or forming the porous material to a size and shape of an end portion or implant.

In accordance with one aspect of the invention, a urethral sling is formed having end portions formed of flexible strands that are woven or knitted in a pattern to bound and define open pores of a mesh. The edges of the end portions include outwardly extending, severed strands of the open pore mesh ("edge extensions") stiffened to maintain their shape and engage with tissue when drawn through a body tissue pathway.

In certain embodiments, a reinforcement may be continuous through the length or substantially the entire length of end portions of open pore material. Alternatively, a reinforcement may be periodic or discontinuous through the length or substantially the entire length of an end portions. Moreover, a continuous or periodic reinforcement may extend laterally across the width of a porous extension portion resulting in treated and untreated lateral bands of constant or varying band widths.

In one preferred embodiment, a reinforcement can be based on heat treatment of an open pore material, by applying thermal energy to solid areas or knitted strands of an open pore mesh, e.g., along edges or in longitudinal or lateral bands of a solid porous material or a mesh. The heat treatment can thermally melt a portion of the material at or adjacent to the outwardly extending edge extensions (e.g., mesh strand ends) sufficiently to stiffen the edge extensions so that upon cooling the edge extensions resist deformation upon contact with tissue. The heat treatment can be performed to a strip of porous material that has previously been cut to produce an edge; or, a sheet of porous material may first be heat-treated and then an edge of an extension portion may be formed at a desired location relative to the heat-treated area, e.g., adjacent to the heat-treated area.

In a further embodiment, a coating of a biocompatible material can be applied from any suitable source to edge extensions of an open pore material to reinforce and stiffen the edge extensions. The coating may be permanent or may be of a biocompatible material that temporarily stiffens the edge extensions and is absorbable during chronic implantation and tissue ingrowth through mesh pores. An absorbable coating may be selectively applied along periodic or intermittent length-wise sections of an end portion, or applied to an entire end portion. The coating may be applied before, during, or after formation of the end portion edge.

In another embodiment, reinforcement can be in the form of a stiffening strand or filament located along and adjacent to edges of an end portion. The stiffening strand or filament can contact or be adjacent to edge extensions, e.g., can be at a first junction or solid area along an end extension edge, and can be held to the open pore material of an edge extension by, e.g., thermal treatment, adhesive, a weave, etc., either periodically or continuously along lengths of end portions.

The various aspects of the invention may be advantageously selectively practiced separately or in any combination.

In one aspect the invention relates to surgical implant comprising an open pore elongate strip. The strip includes an edge comprising edge extensions, and reinforcement adjacent to an edge and not including the edge, the reinforcement causing an increase in the force required to pull the strip through tissue.

In another aspect the invention relates to a surgical implant including an open pore elongate strip having edges with edge extensions. The edge extensions are coated with a stiffening material that increases stiffness of the edge extensions.

In another aspect the invention relates to a method of preparing an implant. The method includes providing an open pore elongate strip comprising edges, and treating the strip adjacent to an edge but not treating the edge, to increase the force required to pull the strip through tissue.

In another aspect the invention relates to a method of preparing an implantable sling. The method includes: providing an open mesh pore elongate strip that includes edges and edge extensions, and coating edge extensions with stiffening material to increase stiffness of the extensions.

In another aspect the invention relates to a method of preparing an implant. The method includes providing a sheet of open pore material, reinforcing a portion of the open pore material to produce a reinforced portion, and cutting the material to produce a reinforced edge extension.

BRIEF DESCRIPTION OF THE DRAWINGS

These and other advantages and features of the described invention will be more readily understood from the following description of preferred embodiments thereof, when considered in conjunction with the drawings, in which like reference numerals indicate identical structures throughout the several views, and wherein:

FIGS. 2 and 2A illustrate exemplary end portions of implants according to the invention.

FIGS. 3 and 3A illustrate exemplary end portions of implants according to the invention.

FIGS. 4 and 4A illustrate exemplary end portions of implants according to the invention.

FIGS. 13A, 13B, and 13C, illustrate a porous material and an exemplary urethral sling prepared from the porous material.

FIG. 14 illustrates exemplary equipment useful for preparing an implant.

FIG. 15 illustrates exemplary equipment useful for preparing an implant.

FIG. 16 illustrates an exemplary processing step of preparing an implant.

Figure 1:
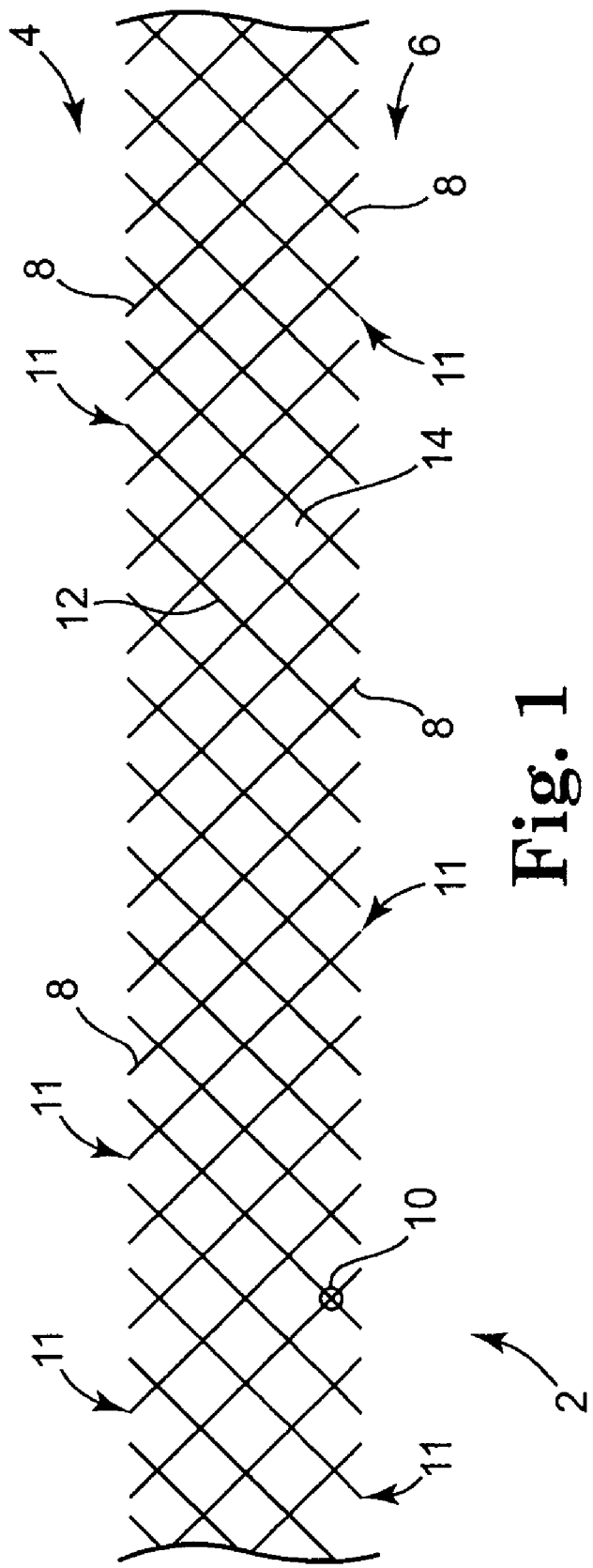
FIGS. 1 and 1A illustrate exemplary end portions of implants according to the invention.

All figures are schematic and not necessarily to scale.

DETAILED DESCRIPTION

In the following description, references are made to illustrative embodiments of methods, devices, systems, and apparatus for carrying out the invention. It is understood that other embodiments and variations of the invention will be recognized and used without departing from the scope of the invention.

The invention can be used with pelvic implants for use in supporting pelvic tissue. Examples include urethral slings configured and particularly suitable for treating stress urinary incontinence (SUI) diagnosed with urethral hypermobility or intrinsic sphincter deficiency in both men and women. A urethral sling or other pelvic implant as described herein can be implanted to treat SUI or other urological disorders such as urge incontinence, mixed incontinence, overflow incontinence, functional incontinence, prolapse (e.g. vaginal), enteroceles (e.g. of the uterus), rectoceles, cystocele, and anatomic hypermobility.

Exemplary implants useful with respect to the invention can be urethral sling implants. These may be of any shape or form, and can be elongated and rectangular for treating SUI. For other treatments, e.g., to provide hammock support for the bladder or bladder neck, or to address a rectocele, enterocele or prolapse, the implant may be any of a wide variety of other shapes and configurations. As an example, a urethral sling may be of the general shape of the slings described and shown in Moir et al., "The Gauze-Hammock Operation", *Journal of Obstetrics and Gynaecology of the British Commonwealth*, Volume 75, No. 1, pps. 1-9 (1968). Thus, as used herein, the terms "urethral sling" and "implant" are used generally to encompass a wide variety of shapes and sizes, materials, and treatments.

Exemplary implants (e.g., urethral slings) can include a central support portion and "extension" portions (or "end portions"), the central support portion being useful to support a specific type of pelvic tissue such as the urethra, bladder, or vaginal tissue. The central support portion can be sized and shaped to contact the desired tissue when installed, e.g., as a sling, and support the pelvic tissue.

End portions connected to and extending from a central support portion can be useful to attach to other anatomical features to provide further support for the central support portion and the supported pelvic tissue. Multiple (e.g., two or four) end portions can extend from the central support portion as elongate "ends," "arms," or "extensions," that are used to attach to other anatomy, such as by extending through a tissue path to an external incision or to an internal anchoring point. See, e.g., US patent publication No. 2005/0080317, having U.S. Ser. No. 10/684,861, filed Oct. 14, 2003, the entirety of which is incorporated herein by reference.

As another example of a urethral sling, a urethral sling may include a widened central support portion to provide increased area of contact between the central support portion of the sling and the tissue being supported, preferably and optionally in combination with a load transfer portion between end portions and the central support portion. See, e.g., Assignee's copending patent Publication No. 2006-0195007-A1, entitled "Transobturator Surgical Articles and Methods," filed on even date herewith, the entirety of which is incorporated herein by reference.

Exemplary pelvic implants can include support portions that can include or consist of a central support portion, two elongate end portions extending oppositely from the central support portion, and a load-transfer portion between an end portion and the central support portion. The implant and the support portions of the implant have a lengthwise direction that is considered to be in the direction of the elongate length of the end portions, and a width that is transverse to the lengthwise direction.

End portions connected to and extending from a load-transfer portion can be useful to attach to other anatomical features to provide support for the central support portion and the supported pelvic tissue. Two end portions can extend from the central support portion as elongate "ends," "arms," or "extensions," that are used to attach to other anatomy, such as by extending through a tissue path to an external incision or to an internal anchoring point, and optionally through the obturator foramen.

Dimensions of an implant can be as desired and useful for any particular installation procedure, treatment, and to support a particular tissue. Dimensions of an exemplary urethral implant for transobturator implantation can be sufficient to allow an end portion to extend from a lateral incision located adjacent to an obturator foramen of a patient, through the obturator foramen, and then to or near a medial incision (e.g., a vaginal incision). An opposite end portion has sufficient length to extend from the medial incision, through the opposite obturator foramen, and to another lateral incision adjacent to the opposite obturator foramen. Length and width tolerances accounts for a range of human anatomy sizes and for an installation procedure.

The central support portion is of sufficient length to at least partially surround a pelvic tissue to support the tissue to treat incontinence, such as to support the urethra (optionally in combination with some or a portion of the length of the load-transfer portions). A width of a central support portion is greater than a width of end portions and is sufficiently wide to increase contact area and frictional forces between a central support portion and a tissue in contact with the central support portion. Exemplary lengths of a central support portion can be in the range from 0.5 to 2 centimeters, such as from 0.7 to 1.8 centimeters. Exemplary widths of a central support portion can be in the range from 1.0 to 4 centimeters, such as from 2 to 4 centimeters.

According to implant embodiments, the combined length of two end portions, a central support portion, and load-transfers portion or portions, can be approximately 16 inches (about 41 centimeters), e.g., within the range from 35 cm to 50 cm. Alternate lengths can also be used.

The width of an implant can be as desired and as useful, consistent with the description herein, including a central support portion that is wider than a width of an end portion. A width of an end portion can be a width useful for implanting the implant and for providing desired strength and fixation properties during and following implantation and optional tensioning of the sling. Typical widths of end portions can be in the range from 0.5 to 2 centimeters, e.g., from 0.8 to 1.5 centimeters. End portions can typically have a uniform or substantially uniform width along the length, normally not varying by more than about 25 percent of the average width along the length of the installed portion of the end portion.

Exemplary implants of the invention can include a central support portion that exhibits a width that is greater than a width of the end portions, e.g., the width of the end portion at a location that is adjacent to the load-transfer portion. A central support portion that has a width that is greater than a width of the end portions can improve contact between the implant and tissue to be supported by the implant. An increased width of a central support portion may take the form of one or two lateral extensions that extends the width of the central support portion in at least one direction (an anterior direction) for contacting tissue that is relatively anterior to a patient's anatomy compared to an otherwise similar central support portion that exhibits a smaller width. Alternately, a central support portion may include two lateral extensions in each of an anterior lateral direction and a posterior lateral direction, to contact tissue that is both anterior and posterior to a central support portion of a relatively more narrow width.

An increased width, e.g., in an anterior direction, can provide for increased contact and frictional engagement between a central support portion and pelvic tissue such as a urethra, bladder neck, vaginal tissue, etc., being supported. A widened central support portion provides a larger area of contact between the sling and a pelvic tissue and can have a reduced tendency to fold or deform upon tensioning of the sling. Increased contact area between a central support portion and pelvic tissue can further allow for improved ability to relocate or approximate tissue if desired during implantation of the sling and treatment and support of pelvic tissue by use of the sling.

Adjacent to a central support portion, and connecting the central support portion to one or preferably to both end portions, can be one or two load-transfer portions. See, e.g., FIG. 13B, pointing out central support portion 222 and load transfer portions 224. Additional examples of slings that include a central support portion and load-transfer portions are illustrated at Assignee's copending patent Publication No. 2006-0195007-A1 entitled "Transobturator Surgical Articles and Methods," filed on even date herewith. The load-transfer portion exhibits a width that is greater than a width of an end portion, such as the width of the end portion at the location at which the end portion connects to the load-transfer portion. The load-transfer portion also includes a width that is less than the width of the central support portion. Functionally, the load-transfer portion allows a load placed across the central support portion, between the end portions, to be distributed across a width of the central support portion that is greater than widths of the end portions.

The dimensions of load-transfer portions can be sufficient to allow for the functional capabilities of a load-transfer portion as described herein, and to allow for overall functional capabilities of an implant. Exemplary dimensions of a load-transfer portion for use as a urethral sling, may include a length extending between an end portion and a central support portion of from about 0.2 to about 2 centimeter, such as from about 0.3 to about 0.7 centimeters. The width of a load transfer portion normally varies between the width of the central support portion (where the load-transfer portion connects to the central support portion), and the width of the end portion (where the load-transfer portion connects to the end portion). The width can increase gradually along the length between the end portion and the central support portion, either in a straight line, a curved or arcuate line, or otherwise, as desired.

A urethral sling may preferably include two load-transfer portions, one connecting each end portion to the central support portion. A load-transfer portion may extend laterally in an anterior direction toward a central support portion that is widened in an anterior direction. Alternately a load-transfer portion may extend bi-laterally in an anterior direction and in a posterior direction, toward a central support portion that is widened bi-laterally in both anterior and posterior directions.

A load-transfer portion may extend between an end portion and a central support portion by a path along an edge that results in a width of a load transfer portion that gradually changes from the width of the end portion to the width of the central support portion. This changing width may define a path, along the edge of the load-transfer portion, that is straight, arcuate, or a combination of straight and arcuate, and that functionally allows a load placed across the central support portion, between the end portions, to be distributed across a width of the central support portion that is greater than widths of the end portions. An advantage of a load-transfer portion as described is that the width of the load-transfer portion, being greater than the width of an end portion, allows for a force applied across the central support portion to be spread out across a greater width of the central support portion (compared to an implant that does not include a load-transfer portion as described herein). Spreading the force to a width that is at least greater than the width of the end portions can reduce or prevent deformation of the central support portion upon placing a force across the central support portion. Deformation can be in the form of "curling" of the central support portion when a load is placed in opposite directions along the end portions.

Materials useful for an implant (e.g., support portion, extension portion, central support portion, etc.) can be any of a variety of synthetic or biologic materials now known or developed in the future. Exemplary end and support portions can be prepared from any combination of synthetic and biologic or natural materials. For example, an end portion or a support portion may be made of a synthetic mesh. An implant of a central support portion and two end portions may be made entirely of a one-piece continuous mesh cut to the size and shape of the central support portion and two end portions. In other embodiments, exemplary end portions can be of synthetic material and a central support portion can be of a different type of a synthetic material or of a biologic material. Components of a multi-piece or multi-material implant may be pre-attached or pre-assembled, e.g., attached during manufacture, so a surgeon is not required to spend significant time cutting, connecting, or otherwise assembling the pieces of an implant prior to a surgical installation procedure.

A synthetic implant material may be in any form, such as a continuous, solid, or semi-continuous (e.g., perforated) film; or in the form of combined fibers or strands, e.g., a braided, knit, tied, mesh, woven, non-woven, or fabric-type of material; or combinations of these. Certain embodiments of implants include a synthetic implant portion in the form of a polymeric mesh material. The mesh material includes one or more woven, knit, or inter-linked polymeric filaments or fibers that form multiple fiber intersections or "junctions" throughout the mesh. The fiber junctions may be formed via weaving, knitting, braiding, knotting, joining, ultrasonic welding, use of an adhesive, or other junction-forming techniques, including combinations thereof, leaving openings or pores ("interstices") between elements of the connected fibers. The size of the pores may be sufficient to allow tissue in-growth and fixation within surrounding tissue upon implantation.

A synthetic implant material can be any synthetic material that can be useful in an implantable surgical device such as a biocompatible polymeric material or a biocompatible non-polymeric synthetic material. Examples of useful polymeric materials that may be useful in a porous material include thermoplastic polymeric materials such as polyolefins (e.g., polypropylenes), polyurethanes, acetal materials, Teflon® materials, and the like; thermoset materials such as silicones; and materials that are otherwise curable, e.g., that can be cured by ultraviolet radiation or chemical reactions, including curable materials such as curable urethanes, epoxies, acrylates, cyanoacrylates, and the like. Any of these materials may be homopolymers, copolymers, or a blend or other combination of homopolymers, copolymers, or both. Other suitable synthetic materials include metals (e.g. silver filigree, tantalum gauze mesh, and stainless steel mesh).

Examples of specific synthetic film and mesh materials are known and may be suitable for use as a portion or piece of an implant such as an end portion or a central support portion. These include biocompatible materials that may be bioabsorbable or non-bioabsorbable, e.g., in the form of mesh materials. Suitable materials include cotton, linen, silk, polyamides (polyhexamethylene adipamide (nylon 66), polyhexamethylene sebacamide (nylon 610), polycapramide (nylon 6), polydodecanamide (nylon 12), and polyhexamethylene isophthalamide (nylon 61), and copolymers and blends thereof), polyesters (e.g., polyethylene terephthalate, polybutyl terephthalate, copolymers and blends thereof), fluoropolymers (e.g., polytetrafluoroethylene and polyvinylidene fluoride), polyolefins (e.g., polypropylene, including isotactic and syndiotactic polypropylene and blends thereof, as well as blends composed predominantly of isotactic or syndiotactic polypropylene blended with heterotactic polypropylene, and polyethylene), silicone, polygalactin, Silastic, polycaprolactone, polyglycolic acid, poly-L-lactic acid, poly-D-L-lactic acid and polyphosphate esters.

Commercial examples of polymeric materials for use in an implant include MARLEX (polypropylene) available from Bard of Covington, R.I.; PROLENE (polypropylene) and PROLENE Soft Polypropylene Mesh or Gynemesh (nonabsorbable synthetic surgical mesh), both available from Ethicon, of New Jersey; MERSILENE (polyethylene terephthalate) hernia mesh also available from Ethicon; GORE-TEX (expanded polytetrafluoroethylene) available from W. L. Gore and Associates, Phoenix, Ariz.; INTEPRO™ polypropylene materials, and the polypropylene material used in the commercially available MONARC™ or SPARC® sling systems, available from American Medical Systems, Inc. of Minnetonka, Minn. Commercial examples of absorbable materials include DEXON (polyglycolic acid) available from Davis and Geck of Danbury, Conn., and VICRYL available from Ethicon.

Suitable non-synthetic (biologic) implant materials include allografts, homografts, heterografts, autologous tissues, cadaveric fascia, autodermal grafts, dermal collagen grafts, autofascial heterografts, whole skin grafts, porcine dermal collagen, lyophilized aortic homografts, preserved dural homografts, bovine pericardium, and fascia lata.

According to embodiments of the described implants, various additional components and features can be incorporated for added utility or convenience, such as components and features that facilitate installation of an implant during a surgical procedure. For instance, a tensioning member (e.g., suture) may be attached to an implant along a portion or entire length of an end portion for use in adding tension or in positioning an implant or a portion (e.g., extension) of an implant. A tensioning suture may be attached at one or multiple attachment points along a length of an end portion. Multiple sutures may be used, such as two or more sutures along a length of one end portion, for added tensioning effect. See, e.g., Assignee's copending United States Patent Publication No. 2006-0195010-A1, entitled "Surgical Implants and Related Methods and Systems," filed on even date herewith, the entirety of which is incorporated herein by reference. Other embodiments of the invention do not require and can specifically exclude a tensioning member such as a suture.

Alternately or in addition, an exemplary implant may include a removable sheath such as a plastic, transparent elongate tube, or the like, that can cover a portion or entire length of an end portion of an implant to facilitate installation by allowing a surgeon to apply tension or pressure on the sheath to indirectly apply pressure or tension to the end portion. Additionally or alternately, end portions of an implant may include a connector or "dilator" tip at an end distal from a central support member, the connector being able to cooperate with an insertion tool (e.g., needle, tunneler, etc.) during a surgical procedure to either push or pull the connector using the end of the insertion tool. For example, a tip may be a rigid plastic tip or dilator constructed to attach to an end of an elongate insertion tool by snapping or otherwise securing to the end of the insertion tool. The tool can then be used to push or pull the connector through a tissue passage to also bring the end portion of the implant through the tissue passage.

Different components of exemplary implants, e.g., support portion, central support portion, end portions, tensioning members (e.g., sutures), etc., can be formed separately and assembled by methods such as those described in pending patent application having U.S. Ser. No. 11/115,655, filed on Apr. 26, 2005, entitled "SURGICAL IMPLANTS AND RELATED METHODS," the entirety of which is incorporated herein by reference.

According to the invention, an implant includes end portions that include side edges ("edges") and edge extensions. The edge extensions exist due to the porous or "open pore" nature of the material used to prepare the end portion. The edge extensions are reinforced to cause the end portion to resist movement within tissue, during implantation, after implantation, or both. Reinforced edge extensions provide increased frictional resistance of an end portion from movement within the tissue, which provides desired short-term fixation properties of end portions within tissue during and immediately after installation, i.e., the ability of the end portions to stick and hold into flesh when installed without moving and potentially without stretching.

Implants described herein can also exhibit desirable long-term fixation properties, e.g., due to mesh becoming in-grown with tissue for the life of the patient. Desirably, an implant such as a urethral sling is capable of experiencing pressure pulses from a patient while still maintaining the position of the tissue that the implant supports, without the implant breaking or experiencing undue elongation or relocation over time.

An end portion can be prepared of any of the synthetic materials discussed above, in particular thermoplastic polymeric materials, and can include pores formed by cutting, molding, or based on a mesh pattern (e.g., weave). The pores may be of any desired shape, such as circular, rectangular, diamond-shaped (symmetrical or non-symmetrical), rhombus-shaped, or formed as interstices of any of these or other shapes based on a weave of thermoplastic strands in a mesh.

An edge extension of an end portion can be considered the extended solid portion, separated by spaces, of an uneven edge of a porous end portion material along the lengthwise edge of the end portion, e.g., that includes severed ends of a mesh or porous film of an end portion separated by spaces. An edge extension can be a portion of an uneven edge of an open pore material that results upon cutting or severing the open pore material along a line that includes adjacent pores, or that is molded or otherwise formed to exhibit an uneven edge profile. An uneven edge can include an edge extension of solid material in the form of a strand, film, sheet, or other extension, etc., interrupted periodically by spaces defined by portions of pores of that material (e.g., holes, fenestrations, interstice etc.), or an open space created by molding an uneven edge.

As an example, FIG. 1 illustrates open pore elongate strip 2, which includes edges 4 and 6, each of which includes edge extensions 8. Strip 2 may be useful, e.g., as an end portion of a surgical implant. The open pore material of strip 2 includes solid portions (e.g., strands) 12 and open pores 14 (illustrated as square or diamond-shaped openings). Strands 12 meet at junctions 10 resulting in porous strip 2 that includes strands 12 crossing and connecting at junctions 10, strands 12 defining the outer bounds of pores 14. In this example, edge extensions 8 are illustrated as portions of material at the uneven edge of an open pore material defined by cutting the open pore material along a line that includes pores. Extensions 8 are the material that remains extending from each junction 10 toward the edges 4 and 6, with severed ends 11 of edge extensions 8 defining edges 4 and 6.

Referring to FIG. 2, another example of an open pore elongate strip, strip 20, includes edges 26 and 28, each of which includes edge extensions 32. Strip 20 may be useful, e.g., as an end portion of a surgical implant. The open pore material includes strands 22 and open pores 24. Strands 22 meet at junctions 30 resulting in porous strip 20 that includes strands 22 crossing and connecting at junctions 30, the strands defining the outer bounds of pores 24. Edge extensions 32 are illustrated as portions of material at the uneven edge of the open pore material defined, e.g., by cutting the open pore material along a line that includes adjacent pores. Edge extensions 32 are the material that remains extending from each junction 30 toward the edges 26 and 28. Ends 31 of extensions 32 define edges 26 and 28.

Referring to FIG. 3, open pore elongate strip 34 includes edges 36 and 38, each of which includes edge extensions 40. The open pore material includes solid portions 42 and open pores 44, defined by solid portions 42. Edge extensions 40 are illustrated as portions of material at the uneven edge of the open pore material defined by cutting or forming the open pore material along a line that includes pores 44. Extensions 40 are the material that extends from the open pore material to define edges 36 and 38. Ends 43 of edge extensions 40 define edges 36 and 38.

Referring to FIG. 4, another example of an open pore elongate strip, 48, includes edges 50 and 52, each of which includes edge extensions 54. The open pore material includes open pores 56 defined by solid portions 58. Edge extensions 54 are illustrated as portions of material at the uneven edge of the open pore material defined by cutting or forming the open pore material along a line that includes pores 56. Extensions 54 are the materials that remain extending from the open pore material to define edges 50 and 52. Ends 53 of edge extensions 54 define edges 50 and 52.

Figure 5:
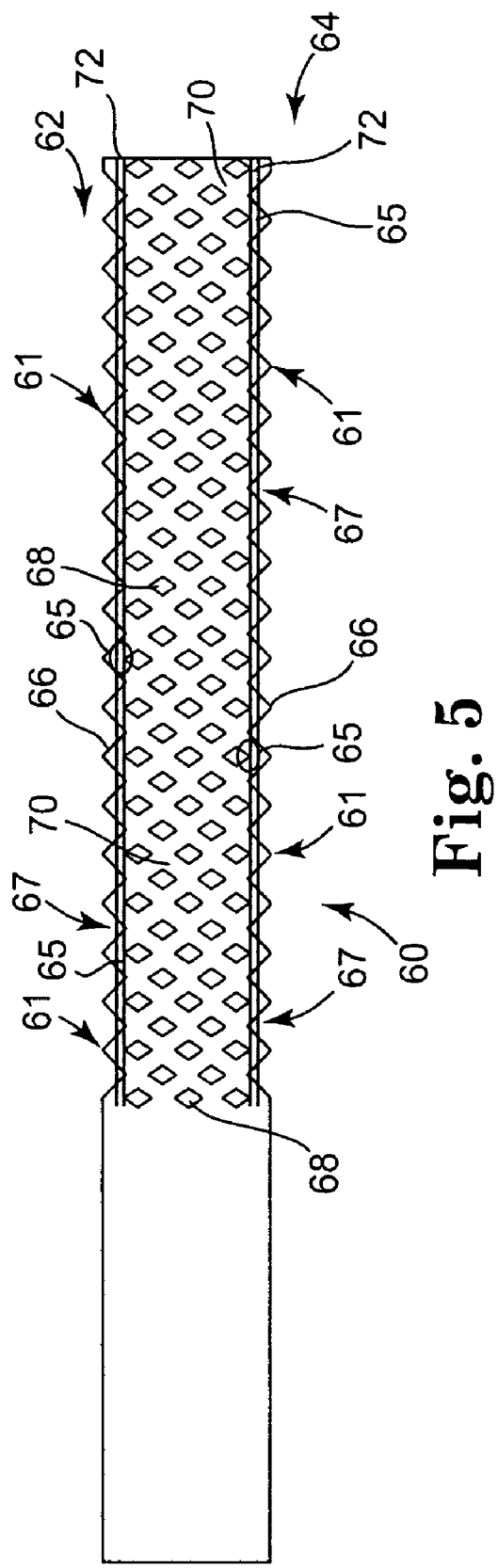
FIG. 5 illustrates exemplary end portions of implants according to the invention.

Referring to FIG. 5, another example of an open pore elongate strip, 60, includes uneven edges 62 and 64, each of which includes edge extensions 66. The open pore material includes open pores 68 defined by solid portions 70. Pores 68 can be prepared as desired, e.g., cut or molded from a continuous film to form an open pore material. In the figure, strip 60 is a film with edges formed (molded or cut) to exhibit uneven edges 62 and 64. Edge extensions 66 are solid portions of material at the uneven edge, interrupted by open spaces 67, the uneven edge being formed by cutting or molding. Ends 61 of edge extensions 66, interrupted by spaces 67, define uneven edges 62 and 64.

Figure 8:
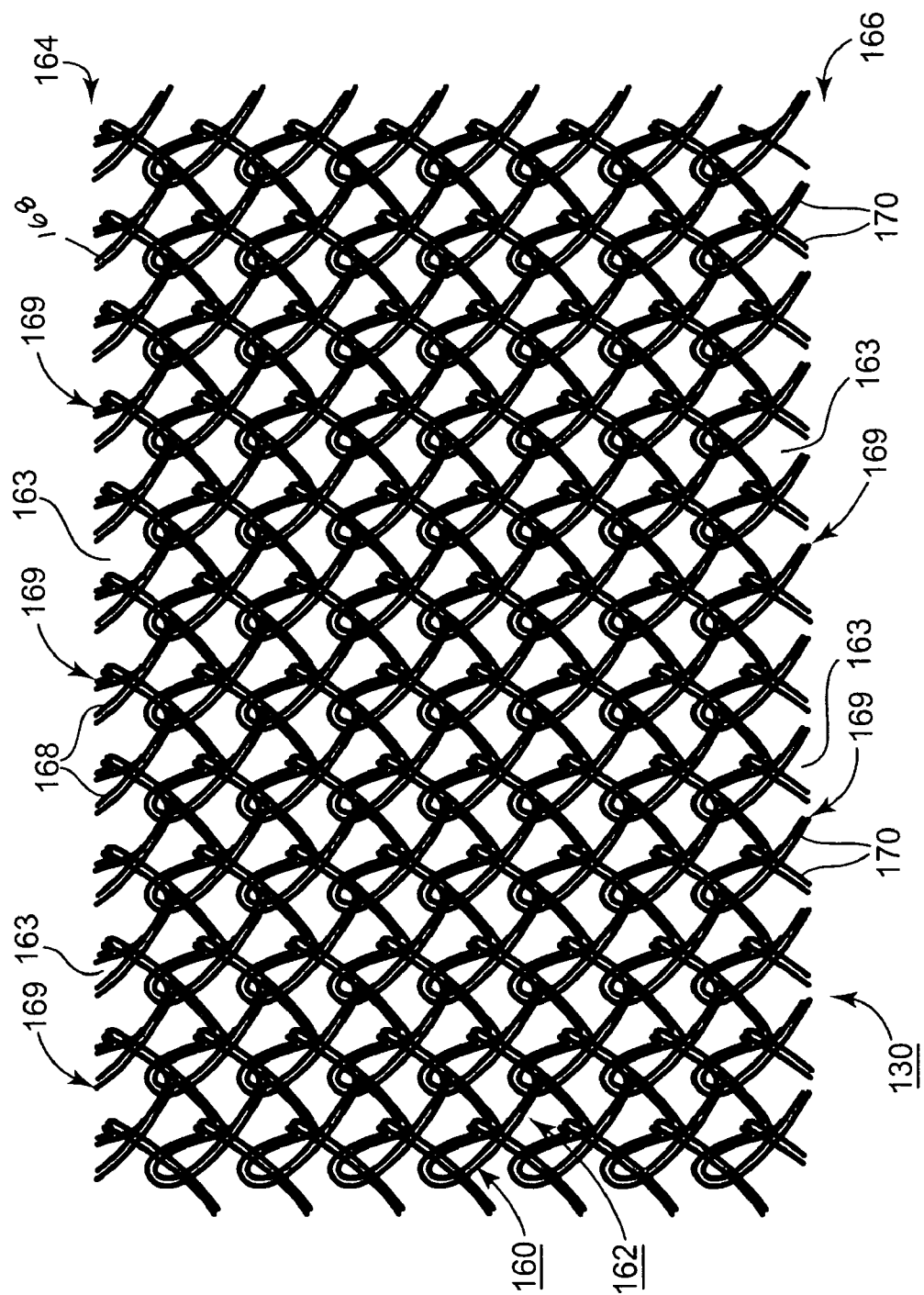
FIG. 8 is an expanded view of a section of open pore mesh.

Referring to FIG. 8, another example of an open pore elongate strip includes edges 164 and 166, each of which includes edge extensions 168 and 170, respectively. The open pore material is a mesh that includes strands 160 and open pores 162. Edge extensions 168 and 170 are portions of strand material 160 at the uneven edge of the open pore material defined by cutting the mesh along a line that includes pores 162. Edge extensions 168 and 170 remain extending from the mesh in the form of small barbs that can dig into flesh. Ends 169 of edge extensions 168 and 170, separated by spaces defined from severed pores, define edges 164 and 166. According to the invention, the mesh can be designed to resist movement through tissue during installation (i.e., "short-term fixation" properties) by, one or more of: maximizing the number, strength, stiffness, or orientation, of these barbs ("edge extension"), and likelihood of the barbs to dig into the flesh and hold the mesh end in place.

According a first type of edge extension reinforcement, edge extensions can be reinforced by reinforcing open pore material adjacent to the edge (e.g., without necessarily treating the edge itself) in a way that limits movement of edge extensions and produces a stiffened edge extension. Other reinforcement can be in the form of a stiffening or reinforcing coating applied directly to edge extensions, optionally also adjacent to edge extensions, to limit the movement of the edge extensions. Reinforcement may also include combinations of treatments or features of edges or of areas of porous material adjacent to edges. Thus, a reinforcement may include or contact an edge (i.e., an end of an edge extension), may be adjacent to an edge but not include the edge (end of edge extension) itself, may contact an edge and an area adjacent the edge, or may contact some portions along an edge of an open pore material and not other portions along the same edge while also including or contacting area adjacent to the edge. With any of these reinforcements, the force required to pull a reinforced elongate strip through tissue can be increased.

A reinforcement that is adjacent to or on the edge should be at the edge or sufficiently close to the edge to cause edge extensions to be reinforced and stiffened so the end portion has increased resistance to movement through tissue. Such reinforcement may be located, for example, on or at the edge extension; at a solid portion of the open pore material that defines or connects to the edge extension (e.g., a junction or a first junction of material forming an end portion); or at a solid portion of the open pore material that defines a first pore of an open pore material from the edge of the material (e.g., a "first junction" or "first solid area"). As an example, a reinforcement may be located at a "first junction" or a "second junction" of an open pore material, which includes a first or a second knot or connection of a woven material or a first or second connection or overlap of strand materials forming an end portion; e.g., a first junction includes a junction between strands or solid areas of an end portion that is closest to the edge of the end portion, generally being the location where an edge extension begins.

A first junction or first solid area of an end portion made of a film or similar non-mesh, non-knit, non-woven open pore material, that is fenestrated, cut, punched, or otherwise formed, is a solid portion of the film material that connects to an edge extension, that defines a space of an uneven edge, and that is the most lateral portion of a an end portion material, near an edge of an end portion, that is not an edge extension.

Without limitation, any useful dimensions between edge extensions, edges, and reinforcement of an extension portion or implant can be used in association with the invention. Reinforcement can be placed at any useful distance from an edge, up to and optionally including the material at an edge. As exemplary values, an extension portion can have a length (measured laterally from the end portion as a distance perpendicular from longitudinal axis of an extension portion) in the range from 0.02 to 0.3 inches, e.g., from 0.05 to 0.1 inches. Reinforcement located adjacent to an edge and not contacting the edge may be located a distance sufficiently close to the edge extensions to produce stiffening of the edge extensions. Typically this location may be at or near a first junction relative to an edge or at a first solid area relative to an edge. In terms of distance, a useful distance from an edge may be in the range from 0.02 to 0.3 inches, e.g., from 0.05 to 0.1 inches, which can coincide with a first junction or a first solid area of an end portion material.

A reinforcement adjacent to an edge may be in the form of any type of material, method, or technique that will improve the strength or stiffness of edge extensions to increase the force required to pass the end portion through tissue. By way of example, a reinforcement may include a material added to or formed or incorporated into an open pore material at a location adjacent to an edge, and optionally not contacting the edge (the end of an edge extension). A reinforcing material may be polymeric or non-polymeric, and may be the same as or different from the material of the open pore material itself. A polymeric material could be a length of interrupted or continuous adhesive, plastic, or thermoplastic materials, or any other polymeric or non-polymeric material that can be incorporated into the open pore material at the described location to stiffen and reinforce an edge extension. A reinforcement adjacent to an edge may alternately or additionally be in the form of a stiffening weave or knot adjacent to an edge, such as a reinforcing weave or knot at a first junction, that is different from knots or weaves at other positions of an end portion.

An exemplary reinforcement may be a strip of continuous or discontinuous solid material such as a stiffening strand that is applied to or that is embedded, formed, or woven, or otherwise incorporated, into an open pore material at a location adjacent to an edge along a length of an end portion. A stiffening strand could be a continuous straight piece of material that is applied by an adhesive, that is molded into a film, or that is woven into a mesh, etc. Examples of suitable stiffening strands could include strands of plastics, bioresorbable materials, thermoplastics, natural materials such as yarns or threads, etc., that are incorporated into an end portion adjacent to an edge.

Another example of a reinforcement adjacent to a strip edge could be a weave of a mesh that includes different weaving or knots at a junction or knot adjacent to the edge, e.g., at a first or second junction relative to an edge.

Still another example of a reinforcement adjacent to an edge of an end portion of an implant is a heat processed area of film or mesh such as a continuous or semi-continuous area of heat-treated film or mesh. Heat treatment may melt a polymeric (e.g., thermoplastic) film, strand, or mesh, to cause the film, strand, or mesh, and any adjacent edge extension, to be strengthened and resist movement, such as at a melted junction or knot of a woven mesh. Exemplary heat treatment may be used to heat treat area of an end portion adjacent to an edge, including one or more of a first junction, a second junction, a strand or solid portion of an open pore material between the first and second junction, a portion of an edge extension, or any other area of an end portion adjacent to an edge.

Figure 1A:
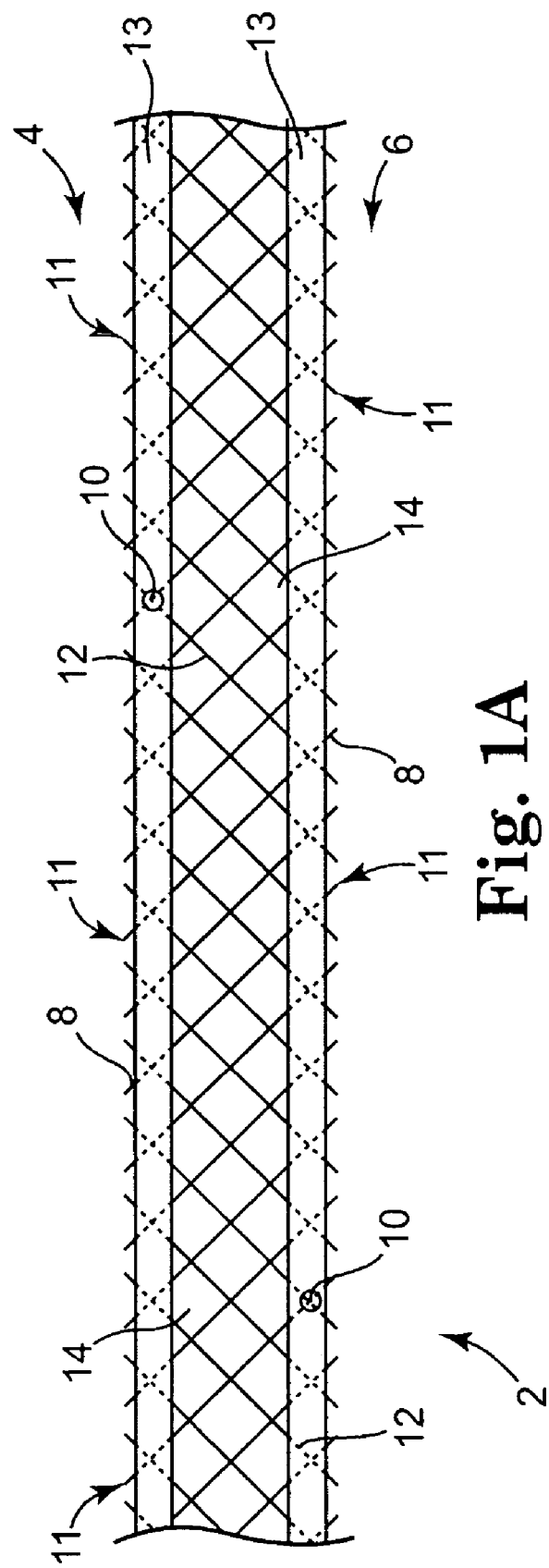

FIG. 1A illustrates an example of an open pore strip having reinforced edge extensions. Open pore strip 2 is as in FIG. 1 with the addition of reinforcing strands or strips 13 located adjacent to each edge 4 and 6. Reinforcing strips 13 may be a material such as a plastic or an adhesive applied to open pore strip 2 as indicated, to cause edge extensions 8 to be stiffened. According to the illustration, strips 11 are placed adjacent to edges 4 and 6 to cover first junctions 10 and a portion of edge extensions 8.

Figure 2A:
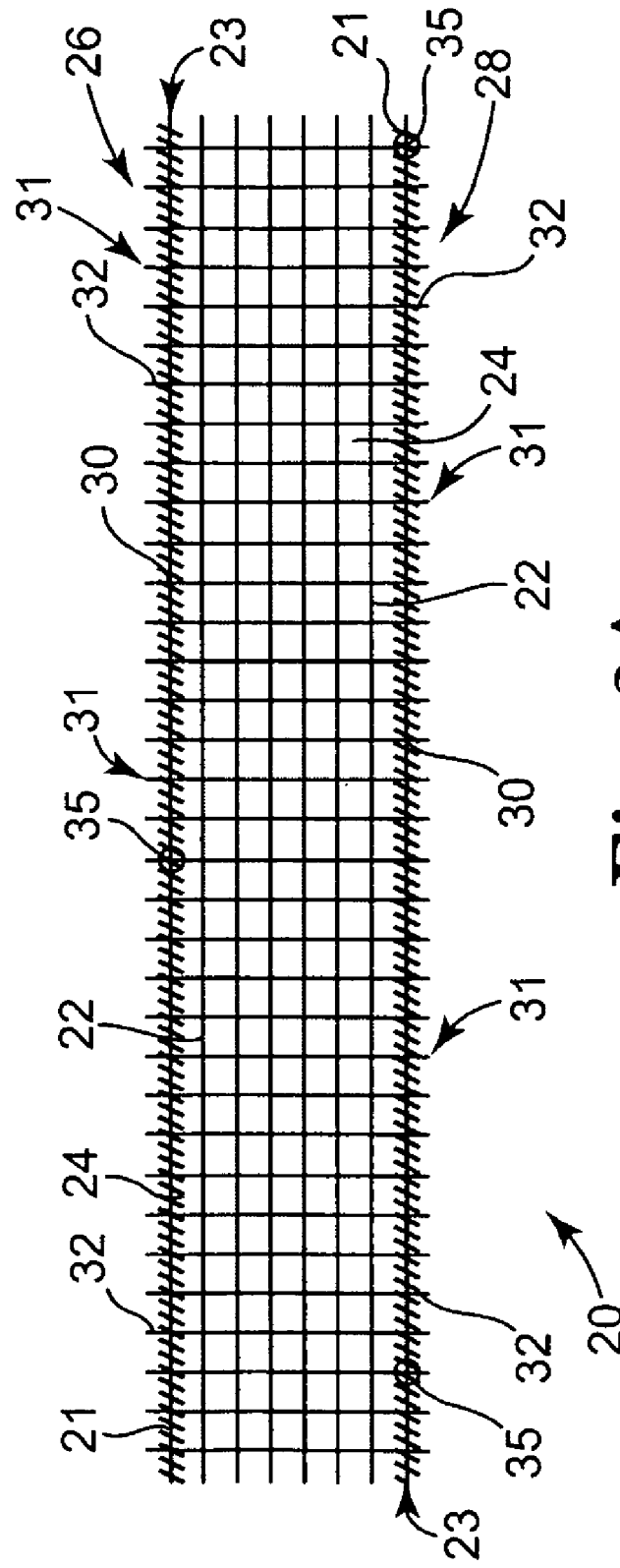

FIG. 2A illustrates another example of a reinforced open pore strip. Open pore strip 20 is as in FIG. 2 with the addition of reinforcing strips 21 located adjacent to each of edges 26 and 28. Reinforcing strips 21 may be a material such as a plastic, an adhesive, a coating of strands or solid material of the open pore material, heat treatment, etc., at the location of strips 20, to cause edge extensions 32 to be stiffened. Reinforcing strips 21 are located along edges 26 and 28 to cover first junctions 35 at the first length-wise solid portion or strand 23 running along each of edges 26 and 28.

Figure 3A:
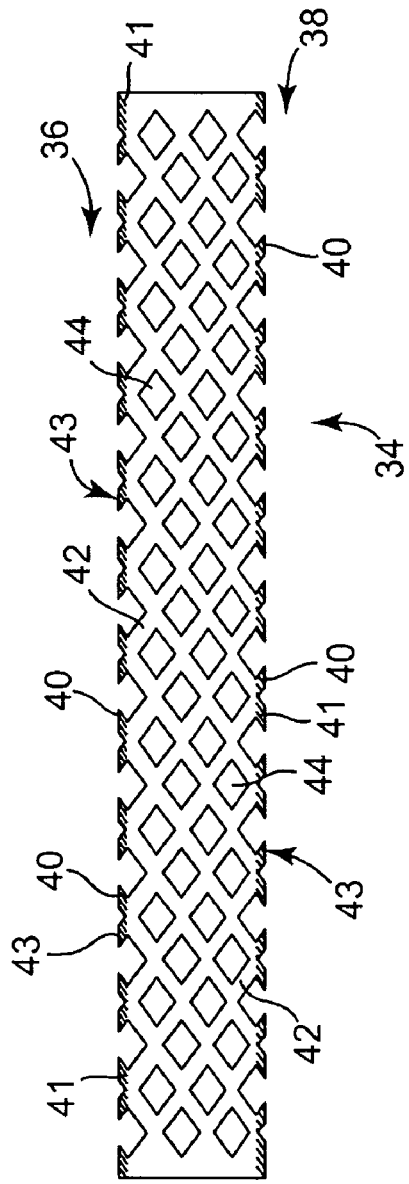

FIG. 3A illustrates another example of a reinforced open pore strip. Open pore strip 34 is as in FIG. 3 with the addition of reinforcement 41 (shaded areas) located at edge extensions 40, including ends 43. Reinforcement 41 is illustrated as shading located on edge extensions 40, at and adjacent to edges 36 and 38. Reinforcement 41 may be in the form of a coated material such as a plastic, adhesive, or another polymeric or non-polymeric material that has been applied to edge extensions 40, including ends 43, as illustrated, to cause extensions 40 to be stiffened. According to the illustration, reinforcement 41 is placed on edge extensions 40, including ends 43 of edge extensions 40, but does not substantially contact the interior solid surfaces 42 located away from edges 36 and 38. In other embodiments it is possible for reinforcement 41 to contact other portions of the open pore material including additional area of solid portions 42. Exemplary widths of coated reinforcement 42, may be any useful width, e.g., up to about 0.3 centimeter or 0.1 centimeter.

Figure 4A:
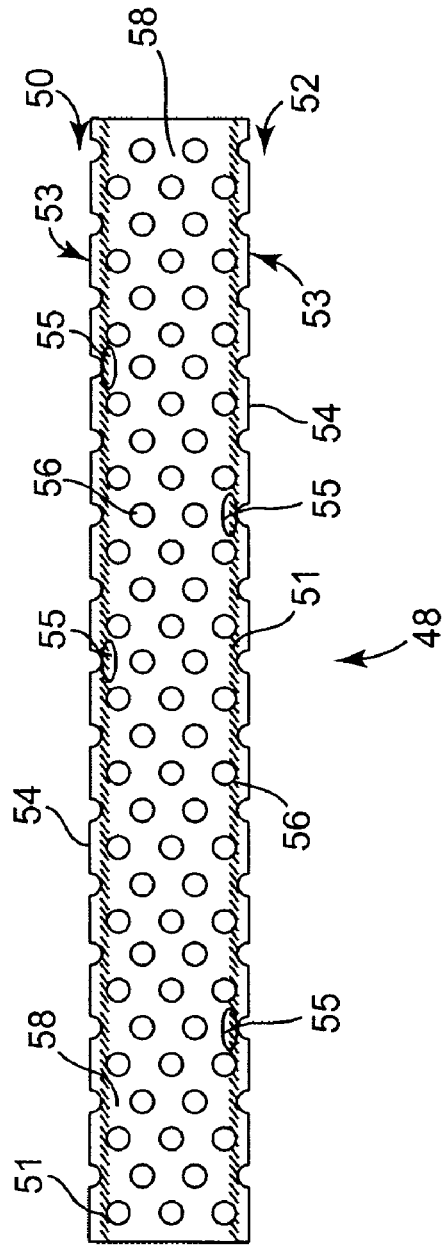

FIG. 4A illustrates another example of a reinforced open pore strip. Open pore strip 48 is as in FIG. 4 with the addition of reinforcing strips 51 located adjacent to each of edges 50 and 52. Reinforcing strips 51, shown as two length-wise shaded strips, may be any reinforcement that can stiffen edge extensions 54. As an example, reinforcements 51 can be reinforced portions of solid portion 58, based on an embedded strip or a thermally processed strip, 51. Alternately, reinforcement 51 may be a material that has been added to the surface of strip 48, such as a plastic or an adhesive applied to the surface of the open pore strip as indicated, to cause edge extensions 54 to be stiffened. Reinforcement 51 is located adjacent to edge extension 54 at a position that includes first solid areas 55. The width of strip 51 and distance from ends 53 can be as useful and as desired, consistent with the current description.

Referring to FIG. 5, open pore elongate strip 60 includes uneven edges 62 and 64, each of which includes edge extensions 66 interrupted by corresponding spaces 67 between extensions 66. Reinforcing strips 72, shown as two length-wise strips adjacent to edge extensions 66, may be any reinforcement that can stiffen edge extensions 66. Reinforcing strips 72 can be embedded strips or a material added to the surface of strip 60, such as a plastic, adhesive, or other coating applied to the surface of the open pore strip as indicated, to cause edge extensions 66 to be stiffened. Reinforcement 72 is adjacent to edge extensions 66 and can be of any useful and as desired width and distance from ends 61, consistent with the current description.

Figure 6:
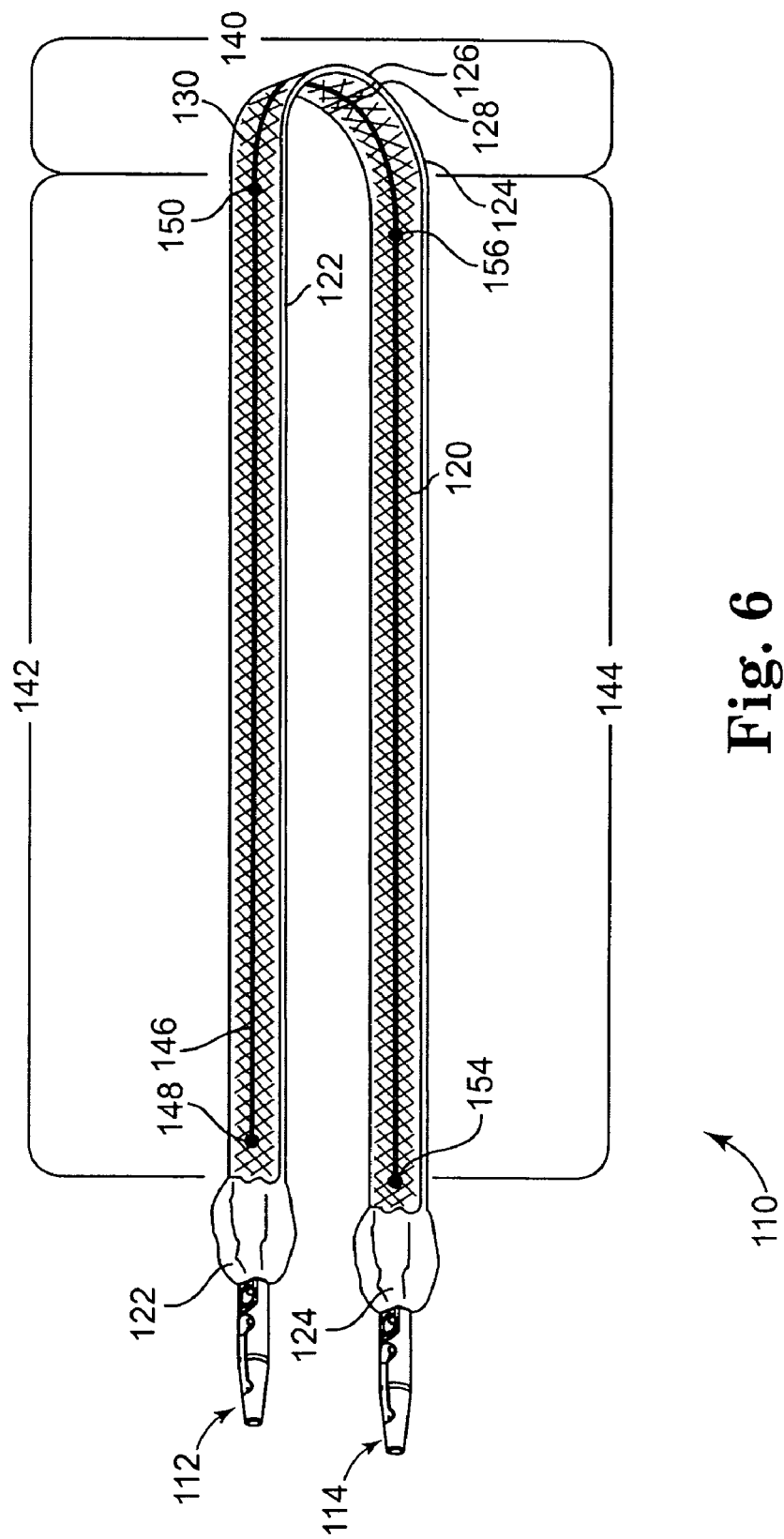
FIG. 6 is a perspective view, in partial section, of an exemplary surgical implant assembly in which the present invention may be advantageously practiced.
Figure 7:
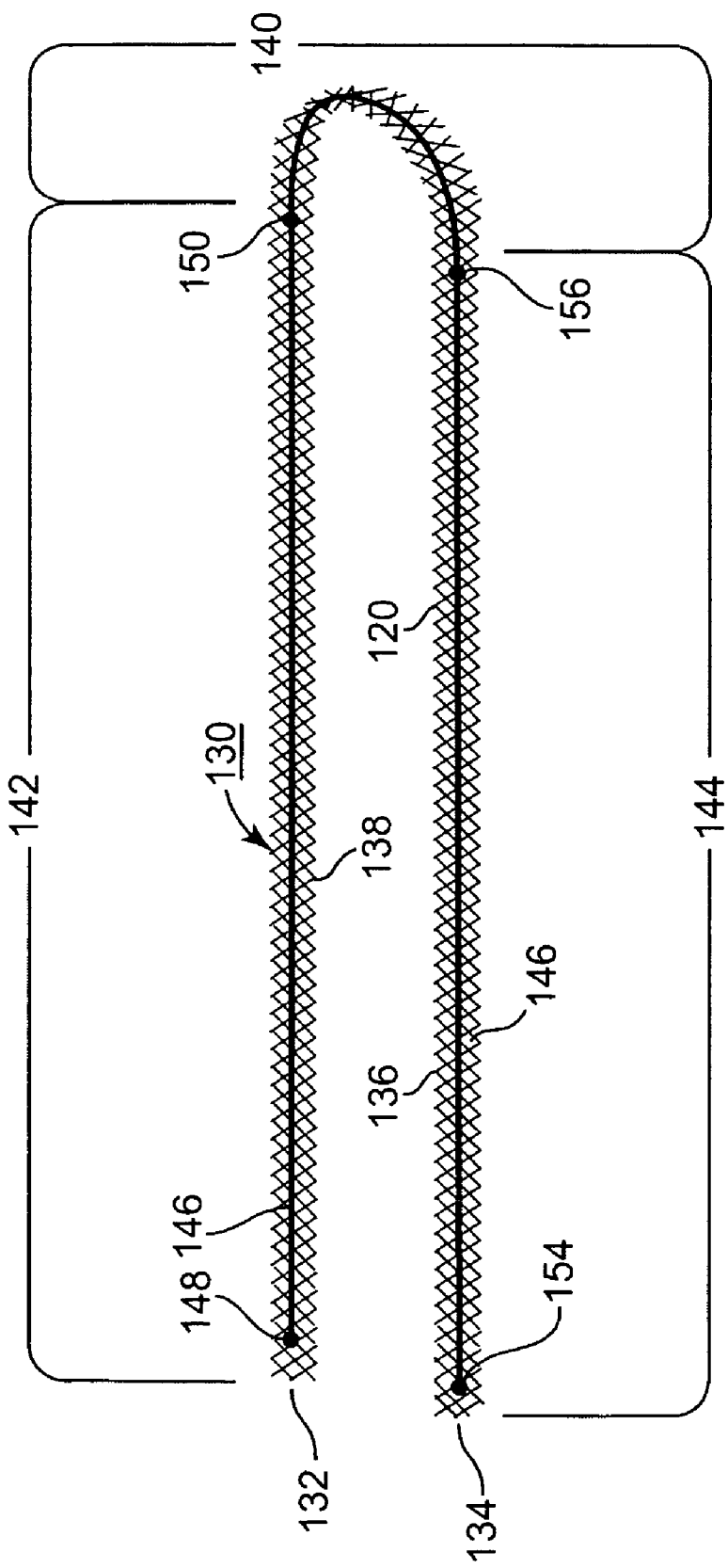
FIG. 7 is a perspective view of an exemplary urethral sling following removal of installation and protective components in which the present invention may be advantageously practiced.

Referring to FIGS. 6 and 7, exemplary embodiments of a urethral sling assembly are depicted. While not specifically illustrated, a sling as illustrated by FIGS. 6 and 7 may include an inventive feature as described herein such as edge extension reinforcement (e.g., a reinforcing coating, reinforcing weave, reinforcing strip or strand, heat treatment, etc.). Elongate urethral sling assembly 110 is designed to treat urinary incontinence. Other pelvic implants for treating other conditions are also contemplated according to the invention to benefit from reinforced edge extensions as described herein. Any such implant may be surgically implanted using presently-known or future-developed techniques, using various delivery systems configured for and techniques that involve transvaginal, transobturator, supra-pubic and pre-pubic exposures or pathways through which at least end portions of a sling or other implant are drawn to dispose a central support portion in operative relation to the urethra, bladder neck, vagina, or other pelvic tissue. The sling assembly of FIG. 6 is depicted as it is supplied or prepared for use in such a procedure.

Sling assembly 110 of FIG. 6 includes two end portions and a central support portion. Sling end connectors ("dilators") 112 and 114, located at the ends of each end portion, can engage free ends of right hand and left hand sling implantation tools (not shown). End connectors 112 and 114 can be shaped to dilate right and left passages through body tissue formed by curved needles of the right and left hand implantation tools in a transvaginal or transobturator procedures, for example.

Sling assembly 110 comprises urethral sling 120 enclosed within protective sheaths 122 and 124 extending from sling end connectors 112 and 114, respectively, to free and open sheath ends 126 and 128, respectively. Open sheath ends 126 and 128 may be overlapped for a short distance within the support portion 140. Preferably, protective sheaths 122 and 124 are constructed of a flexible thin transparent plastic film that enables visual examination of urethral sling 120 and is sufficiently lubricious to pass easily through tissue passageways of a patient formed using sling implantation tools. Sheaths 126 and 128 can include sheath indicia or tear scores, perforations, or holes for assisting a surgeon in orienting urethral sling 110 relative to a urethra. Sling 120 can be left in place chronically following implantation.

Referring to FIG. 7, sling 120 comprises an elongated, rectangular (in this depicted embodiment) braided, woven, or knitted mesh strip or simply "mesh" 130 that extends between mesh ends 132 and 134 coupled to sling end connectors 112 and 114 (not shown in FIG. 7), respectively. Mesh 130 may be continuous throughout the length of urethral sling 120 between mesh ends 132 and 134. At least one optional tension control element or inelastic tensioning suture 146 extends from one suture end 148 attached to mesh 130 proximate sling end connector 112 to a second suture end 154 attached to mesh 130 proximate sling end connector 114. Tensioning suture 146 may take the form of and be tied or otherwise attached to strands of mesh 130 at suture ends 148 and 154, and at tie points 150 and 156 along the length of the tensioning suture 46. Tie points 150 and 156 effectively subdivide urethral sling 120 into central support portion 140, intermediate tie points 150 and 156, and end portions 142 and 144. Central support portion 140 is illustrated to have the same width as end portions 142 and 144, but may be wider or narrower.

Urethral sling mesh 130, tensioning suture 146, and protective sheaths 122 and 124, are made of biocompatible materials having sufficient strength and structural integrity to withstand the various forces exerted upon these components during an implant procedure and following implantation within a patient. Inelastic tensioning suture 146 is adapted to facilitate drawing end portions 142 and 144 through tissue passages to position support portion 140 in relation to the urethra without unduly stretching or distorting mesh 130 of urethral sling 120.

Inelastic tensioning suture 146 may be selected from any known or developed useful materials (e.g., as discussed in the above-referenced U.S. Pat. No. 6,652,450 wherein tensioning sutures are alternatively referred to as tension adjustment or position adjustment members). Accordingly, tensioning suture 146 may comprise a monofilament strand having a round, flattened or other shape cross-section or a strand of, braided, or wound filaments. A strand or filaments may be a biodegradable material, a non-biodegradable material, or a combination thereof. Suitable materials include but are not limited to non-absorbable Deklene™ polymer, Prolene™ polymer, nylon, polypropylene, polyethylene, nylon, polyester, etc., and absorbable, bioabsorbable, and/or resorbable materials, e.g., Monodek™ poly-P-dioxanone, Bondek™ polyglycolic acid (PGA) polymer, poly-L-lactide (PLLA), polyethylene glycol, Mersile™, Teflon™, Gore-Tex™, Silastic™, Marlex™, Vaskutek™, and any combination of such materials. Additional meshes are disclosed in Dietz et al., "Mechanical Properties of Urogynecologic Implant Materials", *Int. Urogynecol. J.* (2003) 14: 239-243; and Iglesia et al., "The Use of Mesh in Gynecologic Surgery," *Int. Urogynecol. J.* (1997) 8:105-115.

Central support portion 140 of urethral sling 130 may alternately be formed of a strip of biocompatible material suitable for chronic implantation that may or may not be resorbable during chronic implantation. Possible materials include allografts, homografts, heterografts, autologous tissues, cadaveric fascia, and fascia lata.

Dimensions of an implant or urethral sling can be as desired. Overall dimensions of assembly 110, including protective sheaths 122 and 124, urethral sling 120, and tensioning suture 146, are sufficient to extend from an external incision at a desired location, e.g., an abdominal incision or an incision adjacent to a patient's obturator foramen, to an undersurface of the urethra, and back to another external incision, with a length tolerance that accounts for a range of human anatomy sizes. According to one implant embodiment, the length of urethral sling assembly 110 is approximately within the range of 52.0 cm to 58.5 cm (20.5 inches to 23.0 inches), the sheath width is approximately within the range of 1.0 cm to 1.63 cm (0.482 inch to 0.642 inch), and sheath material thickness is approximately within the range of 0.127 mm to 0.203 mm (0.005 inch to 0.008 inch), respectively. Mesh 130 preferably has a length, width, and thickness approximately within the range of 49 cm to 51 cm (19.3 inches to 20.1 inches), 1.0 cm to 1.2 cm (0.394 inch to 0.472 inch) and 0.508 mm to 0.711 mm (0.020 inch to 0.028 inch), respectively. Alternate lengths, widths, and thicknesses can also be used.

An enlarged section of exemplary mesh 130 (without tensioning suture 146 and without a reinforcement in accordance with the present invention) is depicted in FIG. 8. Open pore mesh 130 is preferably knitted into a knit fabric (open pore mesh) from a plurality of monofilament or multi-filament strands 160 of one or more polymeric material or materials as described herein, bounding substantially regularly-spaced open pores 162. Open pore mesh 130 can be cut from a bolt or sheet into a substantially planar strip shape of a desired length and width. To produce consistent edges 164 and 166 and edge extensions 168 and 170, a sheet can be cut along aligned centers of selected open pores 162 such that opposed edges 164 and 166 are formed and a substantially constant row of intact partial open pores 163 and edge extensions 168 and 170 are formed to produce uneven edges 164 and 166. Thus, each mesh edge 164 and 166 is characterized by trimmed or cut strand ends 168 and 170 extending substantially outward and away and substantially in the plane of planar strip shaped mesh 130.

An implant as described, e.g., such as that of FIG. 6 or 7, having reinforced edge extensions according to the invention, can be implanted as desired, by any presently known or used method or any method developed in the future, such as by implantation procedures described in the above-referenced '214, '450, and '524 patents and U.S. Patent Application Publication Nos. 2005/0043580 and 2005/0065395.

As a single example, referring to the sling of FIG. 6, sling connector ends 112 and 114 can be fitted to two- or three-dimensional implantation tools, and end portions can be drawn through a tissue passage. Central support portion 140 is adapted to be drawn against tissue to support the urethra or bladder neck after end portions are drawn through body passageways. Sling connector ends 112 and 114 are drawn out of an external incision in the skin of a patient and are detached from the implantation tool needle ends. Mesh 130 and sheaths 122 and 124 are severed just proximal to suture ends 148 and 154, respectively. The remaining portions of sheaths 122 and 124 are withdrawn over mesh 130 and through the external skin incisions. Urethral sling 120 then remains in place, and tension adjustments are made to provide sufficient urethral support or resistance to leakage. The incisions are closed, and tissue ingrowth into the pores of mesh 130 takes place in a matter of weeks.

Open pores of an open pore material, e.g., pores 162 of mesh 130 shown in FIG. 8, can be maintained open following implantation so that tissue ingrowth can occur through open pores 162. Tissue ingrowth can also occur about cut strand ends 168 and 170. However, without reinforcement as described herein, contact with tissue may cause end extensions to be bent inward against the strands bounding and defining the adjoining intact open pores 162. After a conventional urethral sling assembly, such as sling 110 (without reinforcement as described herein), is implanted, and protective sheaths are retracted, tensioning forces can be applied to central support portion 140 to tension the sling by pulling on free mesh ends 132 and 134. The ends of tensioning suture 146 can also be grasped and pulled, but at times, the pulling forces can so distort the shape of mesh 130 as to diminish the effective engagement of the cut strand ends with body tissue. In addition, the surgical use of a sling such as urethral sling 110 (without reinforcement) may sometimes result in severing the sling end connectors 112 and 114 and the respective protective sheaths 122 and 124 so that the tensioning suture 146 is no longer attached to the mesh 130 at the tied tensioning suture ends 148 and 154, and distortion of the mesh can occur as the mesh ends 132 and 134 are pulled.

According to the invention, therefore, an implant such as sling 110 can be reinforced at and adjacent to edges, to improve performance during and after implantation. Open pore mesh 130 of urethral sling assembly 110 of FIG. 6 (for example) can be reinforced along all or part of end portions 142 and 144 to cause the open pore material edges to maintain the outward extension of edge extensions (strand ends) 168 and 170 when mesh 130 of end portions 142 and 144 is in contact with tissue, as when protective sheaths 122 and 124 are removed. Mesh 130 of central support portion 140 does not require reinforcement of edge extensions and reinforcement of edge extensions of central support portion 140 is optional and specifically excluded from certain embodiments of implants of the invention.

Figure 9:
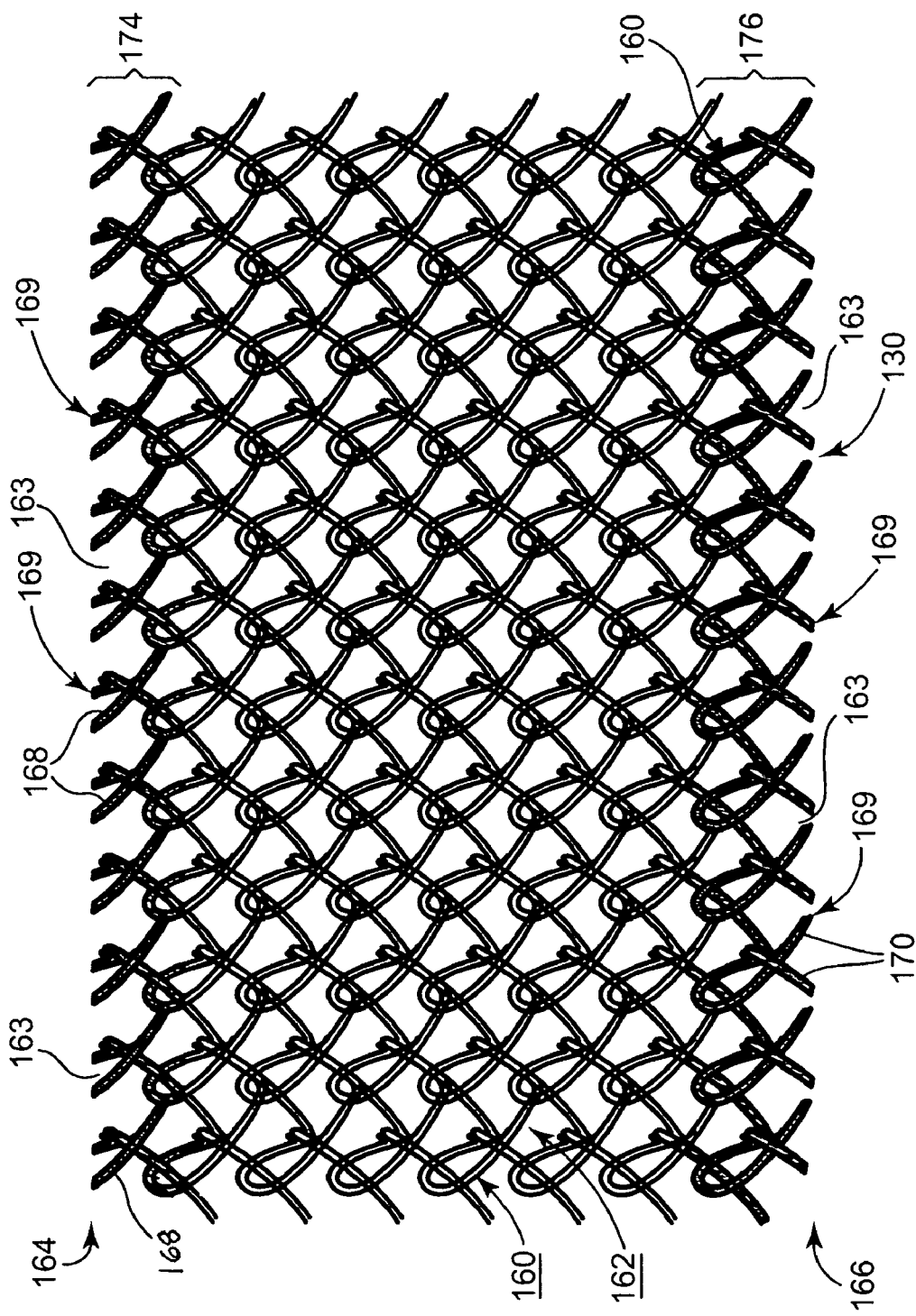
FIG. 9 is an expanded view of a section of open pore mesh of a surgical implant following edge treatment in accordance with an aspect of the invention.

FIG. 9 depicts a section of open pore mesh 130 with edge treatment of edge extensions (severed strands) 168 and 170 in accordance with one aspect of the present invention. In FIG. 9, edge extensions 168 and 170 are reinforced by any one or more of a coating, heat treatment, or other mechanical or chemical treatment that stiffens edge extensions 168 and 170 at locations depicted by edge bands 174 and 176 (shaded areas at edges). Edge bands 174 and 176 may extend in parallel with elongated, substantially centrally disposed tensioning sutures (as illustrated in FIGS. 6 and 7).

Reinforcement as in FIG. 9 may be effected by heat treatment of strands 160 in edge bands 174 and 176 with heat sufficient to fuse the strands 160 together and to fuse strand filaments together, if strands 160 are formed of filaments. A heated press may be used to apply both pressure and heat to edge bands 174 and 176, either before or after cutting or otherwise forming edges 164 and 166 to produce extension portions 168 and 170. Alternately, mesh 130 may be cut to a desired width for an end portion of an implant, and the portion of the mesh 130 between edge bands 174 and 176 may be isolated and thermal energy or a chemical coating may be applied from any suitable source to effect fusing or stiffening of the material located at edge bands 174 and 176. For heat-treating, applied heat and duration of heating is selected to ensure that strands 160 located within edge bands 174 and 176 are fused, and the strand ends 168 and 170 remain stiffened and extending outwardly without disintegrating.

According to other embodiments of reinforcement according to the invention, as also illustrated by FIG. 9, edge bands 174 and 176 can be in the form of a coating of a stiffening coating (either before or after cutting to form edges 164 and 166). A stiffening coating can be applied using any suitable source and method onto edge bands 174 and 176, to coat edge extensions 168 and 170 for stiffening. The coating may be a polymer that permanently stiffens edge bands 174 and 176. Alternately the coating may be of a biocompatible and bioresorbable material that temporarily stiffens the mesh strands that it is applied to, but is soluble and dissolves during chronic implantation and tissue ingrowth through mesh pores 162 and proximal to coated edge extensions 168 and 170.

Suitable soluble materials (described, for example, in U.S. Pat. Nos. 4,827,940, 5,531,783 and 5,716,391) may be selected from among mannitol, dextrose, sorbose, sucrose, or salts, e.g., sodium chloride, potassium chloride, sodium carbonate, and polyvinylpyrrolidone (PVP).

Coating of edge bands 174 and 176 using a reinforcing coating may be by any useful coating or application technique, such as by a continuous method over substantially all or a portion of the lengths of the end portions of an implant.

Reinforced edge bands 174 and 176 may be periodic or continuous along intermittent sections of the length of end portions. The length of periodic edge treatments and the spacing between periodic edge treatments may be either constant or varied. Moreover, a continuous or periodic edge treatment may extend laterally across the width of an end position, resulting in treated and untreated lateral bands of constant or varying band widths. As illustrated in FIG. 9, strips 174 and 176 can include edge extensions 168 and 170 and can also cover the first and second junctions of porous material 130.

Figure 10:
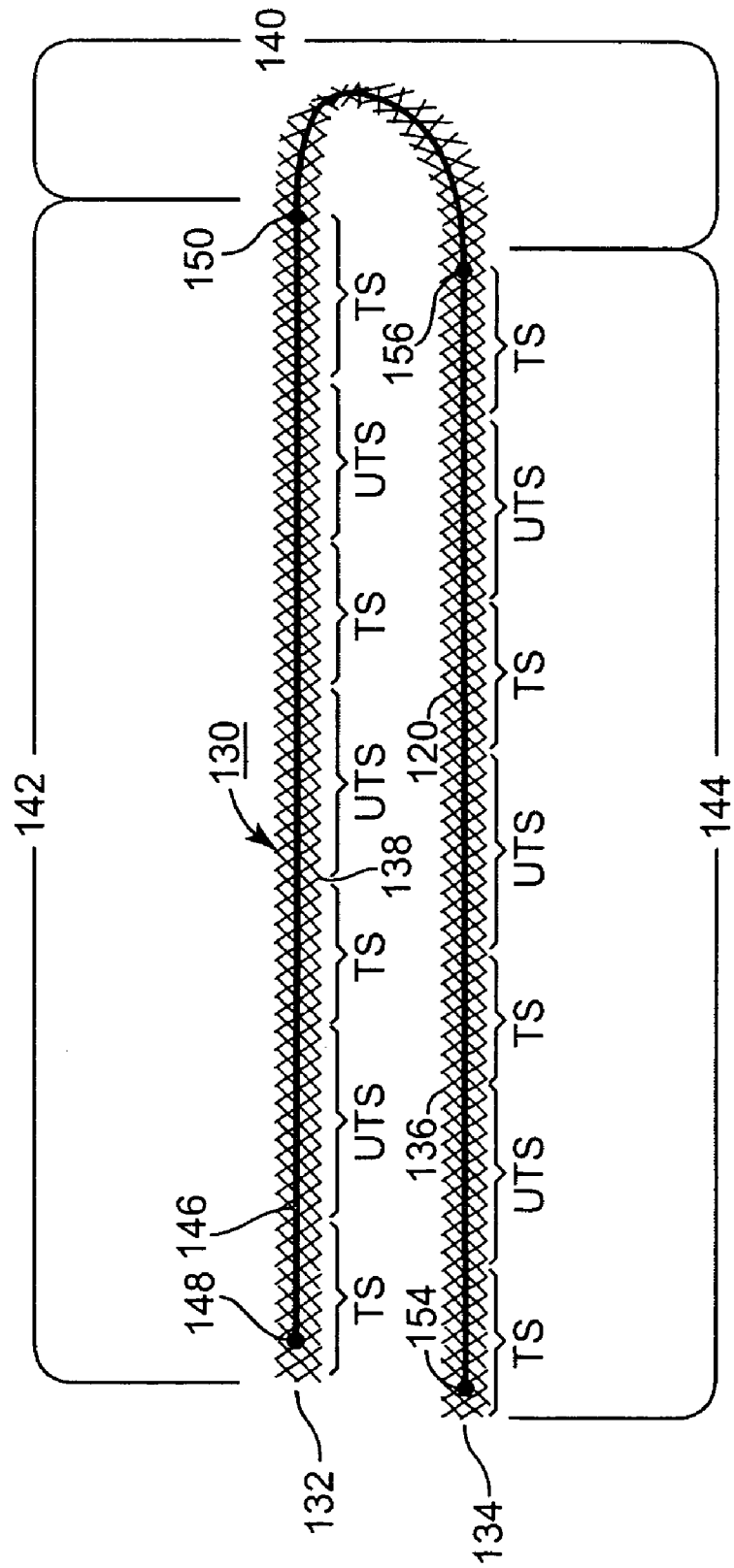
FIG. 10 is a perspective view of an exemplary urethral sling wherein end portions are treated in treated sections and untreated in untreated sections.

According to exemplary embodiments of end portions, end portions such as 142 and 144 may exhibit alternating reinforced mesh sections and non-reinforced mesh sections. The lengths of the alternating reinforced and non-reinforced sections may be the same or may be varied. FIG. 10 generally depicts mesh 130 subdivided into treated sections TS and untreated sections UTS within end portions 142 and 144, wherein a reinforcement may be constrained within edge bands 174 and 176 or extend across the width of mesh 130. In the case of use of soluble coatings to treat mesh 130, it possible to simply coat the entire length or substantially the entire length of mesh 130 including end portions 142 and 144, either before or after forming sling 120 to desired dimensions, e.g., by cutting to form edges and edge extensions.

Figure 11:
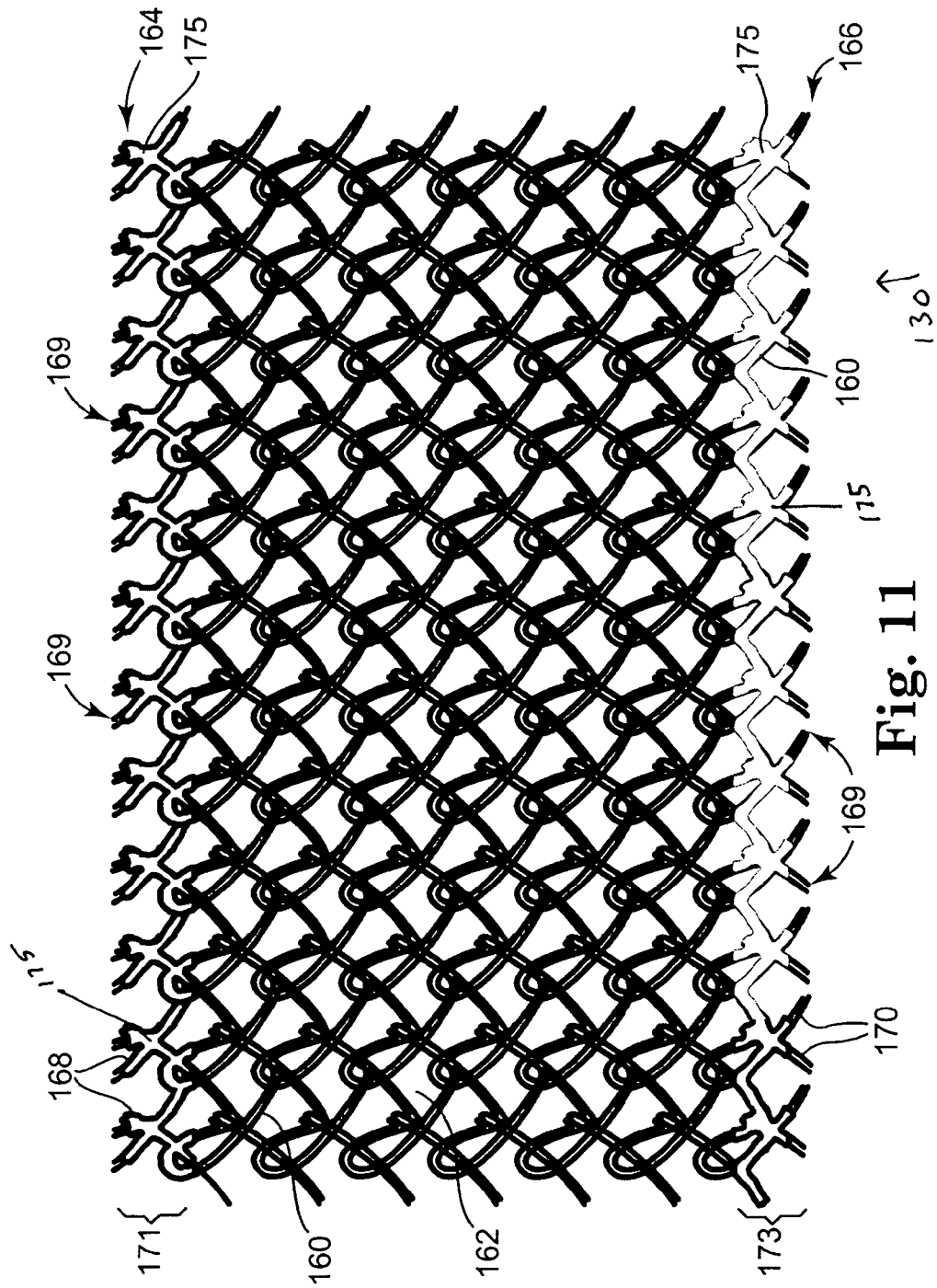
FIG. 11 is an expanded view of a section of open pore mesh of an exemplary surgical implant.

In an alternate embodiment of reinforcement of an open pore mesh, FIG. 11 illustrates an open pore mesh as in FIG. 8, reinforced using thermal treatment of strands 160 at a location adjacent to edges 164 and 166, to stiffen edge extensions 168 and 170. To produce reinforcements 171 and 173 adjacent to edges 164 and 166, pressure and or thermal energy may be applied to mesh 130 at the illustrated locations. These reinforced areas 171 and 173 including first junctions 175, as well as portions of strands 160 that are adjacent to first junctions 175, but do not include ends 169 of edge extensions 168 and 170.

Figure 12:
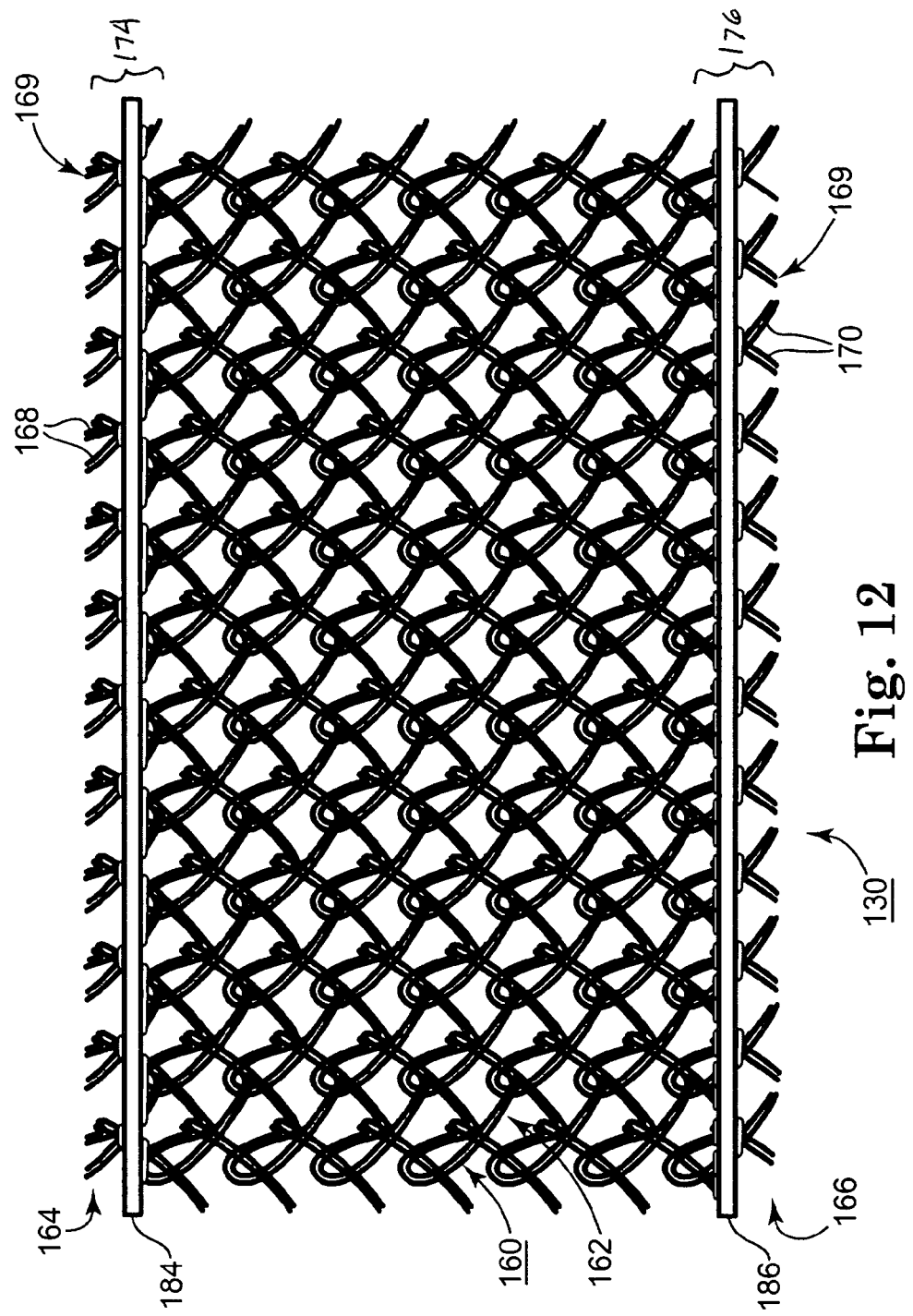
FIG. 12 is an expanded view of a section of open pore mesh of an exemplary surgical implant.

In an alternate embodiment of reinforcement of a an open pore mesh such as that of FIG. 8, FIG. 12 illustrates an open pore mesh as in FIG. 8, reinforced using stiffening strands 184 and 186 located adjacent to edges 164 and 166, to stiffen edge extensions 168 and 170. Individual fibers or filaments that make up edge stiffening strands 184 and 186 may be extruded, woven, braided, spun, knitted, non-woven or have other similar configurations. Mechanical properties of stiffening strands 184 and 186, e.g., tensile strength, elongation at break point, stiffness, surface finish, etc., may be similar to or different from those of strands 160 or a tensioning suture (not shown), and may vary along the lengths of stiffening strands 184 and 186, if desired. Pressure, thermal energy, adhesive, or a combination of these, may be applied to securely place stiffening strands 184 and 186 at the illustrated or other desired location of a porous material, relative to extension portions. Again, a heated press may be used to apply pressure and heat to stiffening strands 184 and 186 in contact with or woven through selected mesh strands 160 or pores 162. Alternately, the portion of the mesh 130 between the edge bands 174 and 176 may be isolated, and thermal energy applied from any suitable source to stiffening strands 184 and 186, within respective edge bands 174 and 176, to effect fusing of stiffening strands 184 and 186 to mesh 130. Optionally, if desired, applied heat and duration of heating can be selected to cause strands 160 of edge bands 174 and 176, or edge extensions 168 and 170, to become melted and optionally fused along with incorporation of stiffening strands 184 and 186 into mesh 130, with edge extensions 168 and 170 remaining stiffened and extending outwardly.

Attachment (e.g., thermal bonding) of stiffening strands 184 and 186 to mesh 130 in the region of the respective edge stiffening bands 174 and 176 may be continuous through substantially all or a portion of the lengths of end portions 142 and 144. Or, attachment of stiffening strands 184 and 186 to mesh 130 may be periodic, i.e., in sections, see e.g., FIG. 10.

Reinforcement of edge extensions can be produced by methods and structures that will be understood, and may use existing or known techniques, or may use techniques that are developed in the future. In general, implants as described that include a reinforcement such as coated edge extensions, heat-treated edge extensions, heat-treated open pore material, a stiffening strand, etc., can be prepared as desired by any useful and effective technique. A reinforcement can be added to an open pore material before, during, or after the open pore material is formed into an end portion, or before, during, or after the end portion is formed into a surgical implant.

In specific with regard to heat treatment, an open pore material may be heat-treated whenever desirable during an overall process of preparing an end portion of an implant. This means, for example, that an end portion of an implant may be formed into a desired size and shape by cutting or molding, such as an elongate rectangle strip having edges and edge extensions, and after formation of the strip by cutting or molding the strip can be heat-treated to produce reinforced edge extensions.

Alternately, an open pore material can be heat-treated prior to being formed into an implant or end portion. Open pore material such as a mesh or porous film can be in the form of a sheet or bolt much larger than the size of an elongate strip useful as an end portion of an implant. The open pore material may be heat-treated while still in the form of a sheet or bolt, and the open pore material may afterward be cut or otherwise formed to a desired size and shape of an elongate end portion for a surgical implant. Generally, the heat treatment step can involve heat treating a desired portion of a sheet of open pore material. In specific embodiments, the heat-treated area will be located adjacent to edge extensions formed upon severing the heat-treated open pore material along a line that includes one or more pores. As such, a heat-treated area can be in the form of a heat-treatment line or narrow elongate strip that extends along a narrow area adjacent to a row of pores of the open pore material, e.g., over a solid portion of the open pore material if a film, or over a weave, knot, or other junction or intersection of strands of a mesh material. Treating an area of open pore material adjacent to pores, then cutting the treated material along a line next to the heat-treated area, can result in an edge of an end portion that includes edge extensions adjacent to reinforced, heat-treated, open pore material.

Figure 13A:
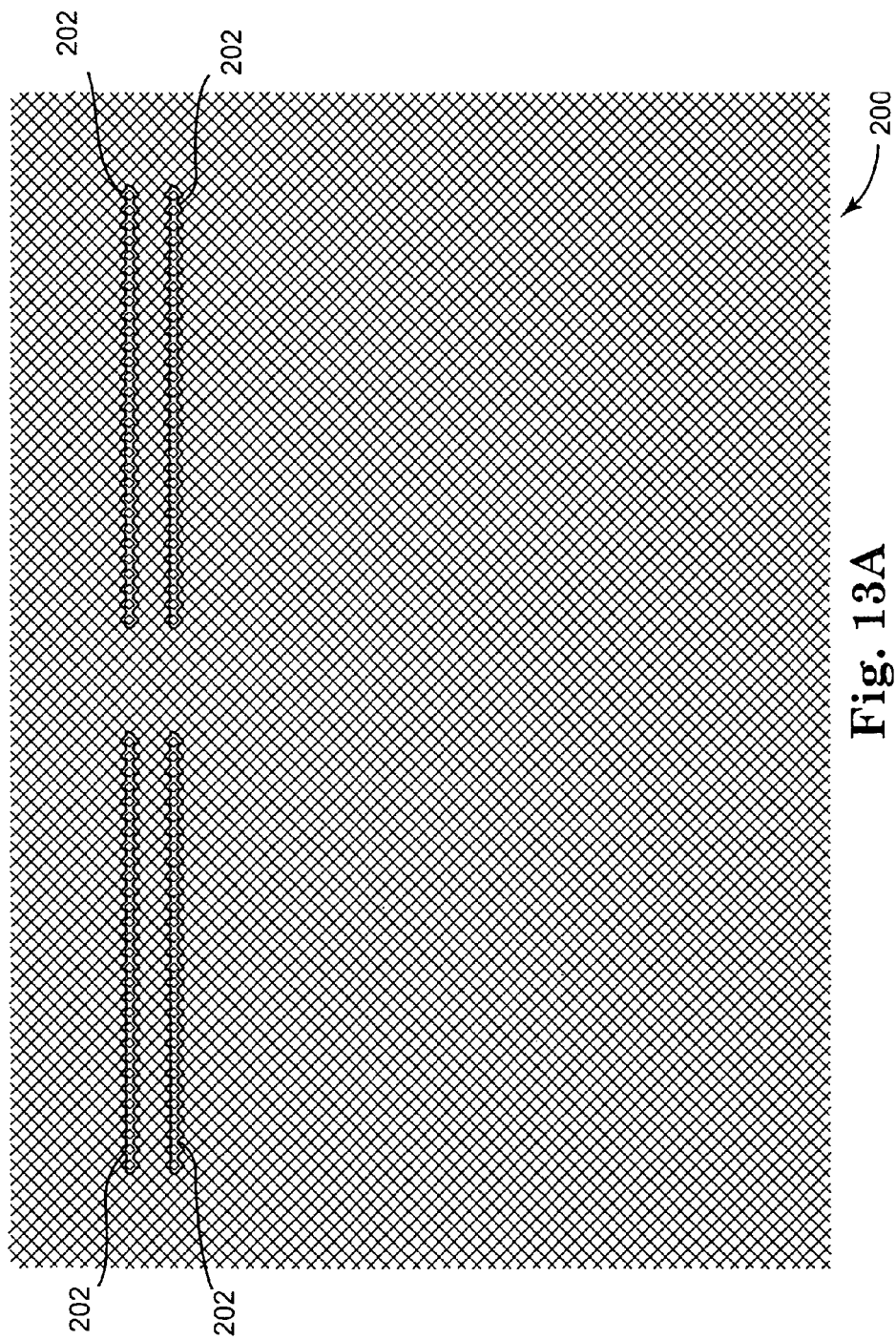

A specific example of a useful method for preparing an implant having reinforced edge extensions based on heat-treatment, is illustrated at FIGS. 13A, 13B, and 13C. FIG. 13A shows a sheet of open pore material 200, which is illustrated as a woven mesh but which may be any open pore material. Mesh sheet 200 is sized substantially larger than the total dimensions of a mesh implant that will be formed from sheet 200.

FIG. 13A illustrates treated (e.g., heat-treated, coated, etc.) open pore material 202. Treated material areas 202 can be in the form of lengths of heat-treated open pore material (e.g., mesh) extending along a desired path of open pore material. As an example, heat-treated open pore material 202 may uniformly contact a longitudinal area that includes a series of adjacent pores along a length of mesh 200. Alternately or in addition, heat-treated material 202 may uniformly contact a longitudinal area that includes a series of adjacent junctions of mesh strands (e.g., knots) or other junctions or intersections of mesh 200. Contacting either a series of adjacent pores or junctions of a porous material can result in a uniform pattern of heat-treated material, e.g., a uniform length-wise area of heat-treated junctions, a uniform length-wise of heat-treated pores, or an area that includes pores and junctions.

In one specific embodiment a heat-treated material 202 includes heat-treated junctions (e.g., knots or weaves) of a mesh material. With a location of heat treatment that includes a heat-treated junction of a mesh, cutting the mesh can be performed along a line that includes open pores that are immediately adjacent to and substantially parallel to the area that includes the series of heat-treated junctions. Upon such cutting step, edge extensions of non-heat-treated severed mesh strands result adjacent to elongate areas of heat-treated mesh junctions.

FIG. 13B illustrates an embodiment of a urethral sling cut from mesh 200 after formation of heat-treated material 202. Urethral sling 210 includes two extension portions 212 extending from central support portion 214. Tensioning sutures 211 extend along the length of implant 210, and are attached at multiple attachment points 213 along the length of suture 211 and implant 210. Extension portions 212 include edges 216 extending at the location of a cut made in mesh 200, following heat-treatment to form heat-treated material 202. Each of edges 216 includes edge extensions 218 and reinforcement in the form of heat-treated material 202. FIG. 13C illustrates a close-up of edges 216, including mesh of extension portion 212, edge extensions 218 in the form of severed strand of un-heat-treated material, and heat-treated material 202 that includes a first row of fiber junctions (e.g., knots) 220 adjacent to edge extensions 218.

Still referring to FIG. 13C, the distance of the reinforcement of edge extensions 218, i.e., heat-treated material 202, from edge 216, can be any distance that stiffens edge extensions 218, and may depend on factors such as the type of mesh, size of connecting strands of mesh, size of knots, and length of edge extensions. For purposes of illustration, the two length-wise strips 202 located along each edge 216 may be at least 0.05 centimeter (measured laterally, perpendicular to the length of the edge) from the severed ends of edge extensions 218, e.g., from 0.1 centimeter from the severed ends of edge extensions 218.

Implants as described may be useful for treating male and female conditions of the pelvic area, such as incontinence and prolapse. Examples of specific pelvic floor disorders are incontinence or stress urinary incontinence (SUI) in both men and women.

A single example of a method for using the described implants, is treating urinary incontinence by surgical implantation of a urethral sling, through a tissue path that traverses the obturator foramen, in men and women. These "transobturator" methods generally involve two lateral incisions, each at a right and left inner thigh of a patient, near a patient's obturator foramen, and a third "medial" incision that can be at the perineal region for men or at a vagina for women. The medial incision can be an external incision in the perineal region in a male, and can be an intravaginal incision in a female. An elongate urethral sling is installed to be located between the medial incision and the two lateral incisions with opposing end portions of the sling traversing each obturator foramen. See, e.g., Assignee's copending United States Patent Application Publication US2003/0171644 (U.S. Ser. No. 10/306,179) filed Nov. 27, 2002, and entitled "Transobturator Surgical Articles and Methods," and U.S. Ser. No. 11/347,047, entitled "Transobturator Methods for Installing Sling to Treat Incontinence, and Related Device," filed on even date herewith, the entirety of each of these being incorporated herein by reference.

The transobturator method involves dissection a tissue path, one on each of the patient's left and right sides, from the lateral incision, through the obturator foramen, and to the medial incision. Three-dimensional tools described herein can produce these tissue paths in either direction. An "outside-in" approach dissects the tissue path by initiating the dissection at the lateral incision and proceeding through the obturator foramen in the direction of the medial incision. An outside-in approach generally will include a next step of attaching an end portion of an implant to the needle distal end and retracting the needle back through the tissue path in the opposite direction of dissection to pull the end portion of the implant back through the tissue path.

The invention also includes surgical kits, assemblies, and systems that include at least one tool, optionally two tools, as described herein. In a preferred embodiment, a kit comprises one or two surgical instruments such as those of FIGS. 1-6, and a polypropylene sling mesh assembly with attached dilators. Such a kit may be provided for the placement of a sling for the treatment of male and female stress urinary incontinence (SUI) resulting from urethral hypermobility and/or intrinsic sphincter deficiency. Exemplary kits may include a tool arranged to provide an ergonomic advantage as described and a urethral sling. In a kit for the male anatomy (or a larger female anatomy) a tool may be sized or shaped with larger dimensions such as a larger width or length of a three-dimensional portion; the sling may be designed for use in the male anatomy with increased strength and short and long-term fixation properties. The sling may be designed, for example, for placement below the CS, may include a widened central support portion, load transfer portions, reinforced edge extensions, multiple sutures, sutures attached at multiple attachment points, etc.

In an alternate implantation method, a variation of a "transobturator" method (considered for the present description to be a "transobturator method") includes a method of inserting an implant through a medial, perineal incision and attaching an end portion of the implant to the obturator membrane. The anchor traverses or otherwise attaches to the obturator membrane. Other features of the inventive methods described herein can be incorporated into such a technique, such as placement of the urethral sling below the BC or CS, approximation of the urethra to improve continence (without the need for compression of the urethra), etc. This method avoids the need for lateral incisions.

In still another alternate embodiment of a transobturator method involving implantation using a needle with a three-dimensional region, single needle may be useful to place left and right end portions both left and right sides of a patient. A single left-handed needle (alternately a single right-handed needle) can be used to place a right side of the sling on a patient's right side, using a transobturator tissue path between a perineal incision and a patient's right-side lateral incision. In the same procedure, the same left-handed needle may also be used to place the opposite end portion on the patient's left side. While the left-handed needle is not optimal for placement at the patient's left side, it can be effective. Systems or kits of the invention can include a single left- or right-handed needle with an implant, for surgical implant according to this method.

A three-dimensional needle for use in the implantation procedure may include a substantially straight spacer portion emerging from an end of the handle portion preferably along the handle axis. This helps afford convenient passage of the needle using an ergonomic wrist roll adopted by some surgeons. The three dimensional needles also include a structure that can be described as a variable spiral portion extending from the distal end of the straight spacer portion. The spiral portion is preferably variable as the angle of the spiral portion changes between the end of the extension portion and the distal end of the needle. The shape of the spiral portions help avoid over-insertion of the needle into the body which helps avoid damage to the sensitive structures in this region of the body. Such needles are described in U.S. Ser. No. 11/347,553, entitled "Needle Design for Male Transobturator Sling" filed on even date herewith, and also U.S. Publication No. 2005/0143618, each of which is incorporated herein by reference.

It will be understood that certain of the above-described structures, functions and operations of the above-described preferred embodiments are not necessary to practice the present invention and are included in the description simply for completeness of an exemplary embodiment or embodiments. It will also be understood that there may be other structures, functions and operations ancillary to the typical surgical procedures that are not disclosed and are not necessary to the practice of the present invention.

In addition, it will be understood that specifically described structures, functions and operations set forth in the above-referenced patents can be practiced in conjunction with the present invention, but they are not essential to its practice.

It is therefore to be understood, that within the scope of the appended claims, the invention may be practiced otherwise than as specifically described without actually departing from the spirit and scope of the present invention.

Example of Method of Preparation of Urethral Sling with Reinforced Edge Extensions Exemplary urethral sling implants according to the invention were prepared according to the following, by the steps, in order, of (1) providing a sheet of mesh material, (2) heat treating the mesh to produce a heat treated area, and (3) cutting the heat treated mesh to form a urethral sling that includes reinforced edge extensions on end portions.

More generally, A step of heat treatment or other placement of reinforcement, and a step of cutting a sheet of material to form an implant or a portion of an implant, may be done in any order, and may be done with different machines or a single machine, e.g., a machine that heat treats and also cuts an end portion, in any order of steps.

Step 1—Heat Treating or "Sealing" Mesh

A sheet of polypropylene knitted mesh was provided for treatment in a heat-treatment or heat-sealing machine. The mesh was of the type used in the MONARC™ and SPARC® female urethral slings used for treating female urinary incontinence, from American Medical Systems, Inc., of Minnetonka Minn. The mesh is that type that includes a "smooth"

side and a "rough" side, as is known. The rough side may have a very slightly more rough feel compared to the smooth side; with reference to the direction of the loop that forms the weave, the loop points slightly more toward the "rough" side surface and slightly away from the "smooth" side surface. The "rough side" is sometimes referred to as the "Technical Face" or "Loop Side" and the "smooth side" is called the "Technical Back" or "Lap Side". The invention can preferably apply heat ("sealing") at the Technical Back side of this type of mesh.

The pores are diamonds that have a size including an approximately 0.060" diameter measured (corner to corner) at the longer dimension and a 0.050" diameter measured in the shorter "width" direction (corner to corner). The sheet has rows of alternating diamonds that face up (the smallest angle point of the diamond faces up) adjacent to diamonds that face down (the smallest angle point of the diamond faces down).

The machine was turned on and set machine to the following cycle parameters:

| | |
|---|---|
| Temp of heated sealing element: | 395° F. (±5° F.) |
| Pressure applied to mesh by sealing element | 35 psi (±5 psi) |
| Time of pressure application | 0.9 sec (±.1 sec) |

The mesh was loaded rough-side-down onto a plate insert that includes a line of several pins that are inserted into the pores of the mesh. The plate insert fits into a groove for positioning the plate and mesh below a heat treating element and a cutting die, for heat treating and cutting at locations of the mesh to produce heat treated reinforcement adjacent to edges, i.e., reinforced edge extensions. A portion of a plate is shown at FIG. 15, which shows plate 300 and pins 302 (not to scale). Pins 302 are not at the center of the width of the plate but are offset from the center, located closer to one side (referred to as the "short side," and indicated with the arrow) than the other side (FIG. 15 shows the offset to an exaggerated degree). The offset is a result of the asymmetry of the "diamond"-shaped pores used to prepare the urethral sling of the present example. The offset of the pins allows a cut of the mesh to align with pore openings as desired, and also allows heat sealing to align as desired, e.g., at a first junction of the mesh.

The mesh is aligned such that the pins of the plate are placed in the same row of pores of a mesh, with the pores being aligned along the length of the end portion as diamond-shapes as opposed to square-shapes (see FIG. 16). More specifically, because the diamonds of are asymmetrical, the diamonds are aligned with an orientation that points the smaller angle of the diamond in a direction away from the "short side" of the plate (indicated by arrows), i.e., the "diamond facing up" pores are held by pins 302. See FIG. 16, which schematically illustrates that pins 302 located to hold a single "row" of upward-facing diamonds 304, of with all diamonds held by pins 302 facing in the same direction.

A "mesh hold-down" piece is used to hold the mesh against the plate. The hold-down is made of Teflon and fits over the mesh and pins of the plate and does not otherwise interfere with the heating element contacting the mesh.

Load the mesh and plate into the heat seal machine, making sure the mesh is laying flat. Initiate heat treatment cycle with the parameters identified above.

Remove Mesh Hold-Down.

Step 2—Die Cutting the Sling

A pneumatic press, cutting die, plate insert and attached mesh (above) are provided. The die includes a blade that is shaped like a one-piece urethral sling, with the following dimensions, as shown in FIG. 14.

| Dimension | Measured Value |
|---|---|
| A | 0.44" |
| B | 0.44" |
| C | 1.4" |
| D | 14" |
| E | 0.58" |
| F | 1.5" |

The pneumatic press is set to 55 psi (±5 psi).

The plate with the mesh on it is placed into the cutting die. This lines up the cut to be adjacent to the heat-treaded portion of the mesh.

The die and mesh are placed in to the pneumatic press and the stamping cover with the plastic side down is placed on to the die.

The press is activated to cut out the sling.

If any strands of the sling did not cut, a pair of scissors can be used to separate the sling from the mesh panel along the cutting line of the die.

If necessary, edges of the sling may be cleaned with a bristled brush to remove any loose sling material.

The invention claimed is:

1. A surgical implant comprising an open pore elongate strip, the strip comprising
   two edges comprising edge extensions, and
   reinforcement comprising lines of heat treated strip adjacent to the edges and not including the edges, the reinforcement causing an increase in the force required to pull the strip through tissue,
wherein the implant is adapted to be implanted in contact with body tissue, the implant comprising:
   a central support portion,
   the open pore elongate strip comprising open pore mesh having opposed mesh edges and formed of strands arranged to define mesh pores, strand ends extending outwardly of the opposed mesh edges as edge extensions; and
   melted strands of mesh adjacent to un-melted edge extensions.

2. A surgical implant comprising an open pore elongate strip comprising two opposing surfaces and edges having edge extensions, the edge extensions coated with a stiffening material that increases stiffness of the edge extensions, the strip comprising un-coated area on at least one surface between the coated edge extensions of the at least one surface.

3. The surgical implant of claim 2, wherein the coating comprises a biodegradable polymer.

4. A surgical implant according to claim 2, adapted to be implanted in contact with body tissue, the implant comprising:
   the open pore elongate strip comprising resilient open pore mesh having opposed mesh side edges and formed of strands arranged to define mesh pores adapted to enable tissue ingrowth therethrough, the elongate strip exhibiting strand ends extending outwardly of the opposed mesh side edges; and
   a coating of stiffening material applied to the outwardly extending strand ends to stiffen the outwardly extending strand ends to resist deformation when placed in contact with tissue, wherein the stiffening material comprises a soluble material selected from the group consisting of mannitol, dextrose, sorbose, sucrose, sodium chloride, potassium chloride, and sodium carbonate.

5. The implant of claim 4 wherein the stiffening material comprises a soluble material selected from the group consisting of dextrose, sorbose, sodium chloride, potassium chloride, and sodium carbonate.

6. A method of preparing an implant, the method comprising:
providing an open pore elongate strip comprising edges,
heat treating material of the strip along a line adjacent to an edge to cause edge extensions to be stiffened and thereby increase the force required to pull the strip through tissue, wherein
the open pore elongate strip comprises a mesh and the edge extensions comprise severed mesh strand, and
the method comprises thermally treating mesh adjacent the edge extensions without melting the edge extensions.

7. A method of preparing an implantable sling, the method comprising:
providing an open mesh pore elongate strip comprising two opposing surfaces, edges and edge extensions,
coating edge extensions with stiffening material to increase stiffness of the extensions, while leaving uncoated area on at least one surface between the coated edge extensions of the at least one surface.

8. The implant of claim 7, wherein the stiffening material comprises a soluble material selected from the group consisting of mannitol, dextrose, sorbose, sucrose, sodium chloride, potassium chloride, and sodium carbonate.

9. The implant of claim 7 wherein the stiffening material comprises a soluble material selected from the group consisting of dextrose, sorbose, sodium chloride, potassium chloride, and sodium carbonate.

10. A method of preparing an implant, the method comprising:
providing a sheet of open pore mesh material,
reinforcing a portion of the open pore mesh material with reinforcement selected from the group consisting of: a reinforcing weave, a reinforcing elongate strand, a strip of adhesive, and melted mesh material, to produce a reinforced portion, and
after reinforcing, cutting the material to produce an elongate mesh strip having edges with reinforced edge extensions, wherein cut edges include edge extensions of severed mesh strands adjacent to the reinforcement.

11. The method of claim 10, wherein the reinforcement comprises a length of melted mesh material aligned with open pores of the open pore mesh material.

12. A surgical implant comprising an open pore elongate strip comprising edges having edge extensions, the edge extensions coated with a stiffening material that increases stiffness of the edge extensions, the stiffening material selected from the group consisting of mannitol, dextrose, sorbose, sucrose, sodium chloride, potassium chloride, and sodium carbonate.

13. The implant of claim 12 wherein the stiffening material comprises a soluble material selected from the group consisting of dextrose, sorbose, sodium chloride, potassium chloride, and sodium carbonate.

* * * * *